United States Patent [19]

Kugele

[11] 4,062,881

[45] Dec. 13, 1977

[54] SULFIDE CONTAINING TIN STABILIZERS

[75] Inventor: Thomas G. Kugele, Cincinnati, Ohio

[73] Assignee: Cincinnati Milacron Chemicals, Inc., Reading, Ohio

[21] Appl. No.: 492,969

[22] Filed: July 26, 1974

[51] Int. Cl.$^2$ ............................ C08H 3/00; C07F 7/22
[52] U.S. Cl. ............................ 260/399; 260/45.75 S; 260/429.7
[58] Field of Search ............ 260/429.7, 399, 410.6

[56] References Cited

U.S. PATENT DOCUMENTS

| | | | |
|---|---|---|---|
| 2,731,482 | 1/1956 | Stefl | 260/429.7 |
| 2,731,484 | 1/1956 | Best | 260/429.7 |
| 2,809,956 | 10/1957 | Mack et al. | 260/429.7 X |
| 2,870,119 | 1/1959 | Leistner et al. | 260/45.75 |
| 2,870,182 | 1/1959 | Leistner et al. | 260/429.7 |
| 2,914,506 | 11/1959 | Mack et al. | 260/429.7 X |
| 3,565,930 | 2/1971 | Kauder | 260/429.7 |
| 3,565,931 | 2/1971 | Brecker | 260/429.7 |
| 3,576,785 | 4/1971 | Weisfeld | 260/45.75 S |
| 3,640,950 | 2/1972 | Weisfeld | 260/45.75 K |
| 3,665,025 | 5/1972 | Wowk | 260/429.7 |
| 3,758,537 | 9/1973 | Wowk | 260/429.7 |
| 3,775,451 | 11/1973 | Brecker | 260/429.7 |
| 3,778,456 | 12/1973 | Hoye et al. | 260/429.7 |
| 3,869,487 | 3/1975 | Kugele et al. | 260/429.9 |
| 3,970,678 | 7/1976 | Molt | 260/429.7 |

FOREIGN PATENT DOCUMENTS

| | | | |
|---|---|---|---|
| 1,226,218 | 3/1971 | United Kingdom | 260/429.7 |

Primary Examiner—Helen M. S. Sneed
Attorney, Agent, or Firm—Cushman, Darby & Cushman

[57] ABSTRACT

A polyvinyl chloride resin stabilizer is provided having a high concentration of tin, in the range from about 10% to about 42% by weight, and a high concentration of sulfur, within the range from about 8% to about 42% sulfur, comprising at least one monoorganotin or diorganotin mercapto alkanol carboxylic ester (or mercapto alkyl carboxylate), mono or poly sulfide and preferably mixed monoorganotin and diorganotin mercaptoalkyl carboxylic acid ester sulfides, especially having 4 to 50% of the diorganotin compound. Polyvinyl chloride resin compositions are also provided, containing these compounds.

61 Claims, No Drawings

SULFIDE CONTAINING TIN STABILIZERS

The present invention relates to noval organotin mercaptoalkyl carboxylic acid ester sulfides useful as stabilizers for polyvinyl chloride and other halogen containing polymers.

As used in the present specification and claims the term mercaptoalkyl carboxylic acid ester means that the alcoholic group is esterified with the carboxylic group. The compounds can also be called mercaptoalkanol carboxylic esters (or mercaptoalkyl carboxylates). Thus, for example, a typical starting ester for making the organotin compounds of the invention is mercaptoethyl caprylate of the formula:

which is in contrast to the starting ester isooctyl thioglycolate having the formula:

used, for example in Kauder, U.S. Pat. No. 3,565,930 and Brecker U.S. Pat. No. 3,565,931. Thus, in the starting compounds used in the present invention the free mercapto group which reacts with a tin compound in the formation of the compounds of the invention is on the alcohol part of the ester whereas in Kauder or Brecker it is on the acid part of the ester. This is an important distinction because the compounds of the present invention have significant advantages over those of Kauder or Brecker. In the first place, they have superior stabilizing properties for vinyl chloride polymers and other halogen containing polymers. While this is noted in laboratory dynamic mill tests, it is even more marked in actual extruder runs. They have greater shelf stability than the corresponding alkylthioalkanoates. The organotin mercaptoalkyl carboxylates taught here have a great advantage over the organotin alkylmercapto carboxylates in that the stabilizers have greater shelf-life or resistance to precipitation. While not being limited to any theory, the instability of the alkylmercaptocarboxylates is attributed to hydrolysis of the ester function with consequent formation of organotin mercapto carboxylate ring or polymeric material, which precipitates. This is in turn attributed to the tin nucleophilicity of the pendant carboxylate anion. With the mercaptoalkyl carboxylates, however, nucleophilicity of the pendant alcohol oxygen is not sufficient to promote displacement of mercaptoalkylalkanoate to form an insoluble ring or polymeric-type product.

Samples exposed to air saturated with water vapor at 100° F have shown very slight haze formation with the organotin alkylmercapto carboxylates, while stored under the same conditions the corresponding alkylthioalkanoates show voluminous precipitates.

The details of the shelf stability test are as follows:

Fifty gram samples were stored in open 2-ounce narrow mouth bottles in a closed desiccator which contained a ½ inch layer of water on the bottom. The desiccator was placed in an oven and the temperature was cycled, 5 days at 100° F and 2 days at room temperature (50°–70° F). The extent of the test was 60 days. At the end of this period about 50% of the alkylthioalkanoate had precipitated while in contrast only about 1% of the mercaptoalkylalkanoate had precipitated.

The alkylthioalkanoate and mercaptoalkylalkanoate used in the test had the following structures:

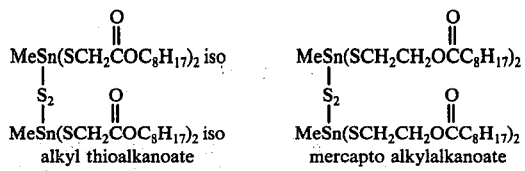

The compounds of the present invention also have reduced odors in comparison with the compounds of Brecker or Kauder.

It is important to have the sulfide group present to obtain the outstanding stabilizing properties. Thus, the products of the invention are superior stabilizers for example to organotin products which are made by reacting methyltin trichloride (or dimethyltin dichloride) with 2-mercaptoethyl caprylate, which latter type of tin compounds are embraced within the broad disclosures of Stefl, U.S. Pat. No. 2,731,482; Best U.S. Pat. No. 2,731,484; Leistner, U.S. Pat. No. 2,870,119; and Leistner, U.S. Pat. No. 2,870,182.

The compounds of the present invention can be described as monoorganotin and/or diorganotin mercaptoalkyl carboxylate monosulfides and/or poly sulfides useful as stabilizers for improving the resistance to deterioration of vinyl chloride polymers (e.g., vinyl chloride resins) when heated at 350° F. having at least two tin atoms linked together only through sulfide sulfur and having tin atoms linked to said tin atoms one to two hydrocarbon groups, (e.g., alkyl, aryl, cycloalkyl, aralkyl or alkenyl having from 1 to 20 carbon atoms) and linked to the tin through carbon, at least one mercaptoalkyl carboxylic acid ester group linked to tin through the sulfur of the mercaptoalkyl group, the organotin compound having an amount of tin within the range from 10 to 42% by weight and an amount of sulfur within the range from 8 to 42% by weight.

The mercaptoalkyl or mercapto hydroxyalkyl group generally has at least two carbon atoms and usually not over 6 carbon atoms. Preferably it has 2 to 3 carbon atoms and more preferably is devoid of hydroxy, i.e., it is mercaptoethyl or mercaptopropyl. However, there can be used hydroxyl containing compounds, e.g., derivatives of monothioglycerol such as monothioglycerine monoacetate, monothioglycerine monostearate as well as compounds such as monothioglycerine distearate, monothiopentaerythritol triacetate, monothiopentaerythritol tristearate, monothiopentaerythritol diacetate.

The sulfides can be mono or polysulfides, e.g., having 1, 2, 3, 4, 5, 6, 10 or more sulfur atoms linked together but preferably are mono to tetrasulfides, most preferably mono to disulfides.

The preferred hydrocarbon radical attached to the tin atoms is methyl.

For atoms as stabilizers most preferably there are used a mixture of monoorganotin compounds and diorganotin compounds of the invention especially mixtures having 96 to 50% of monoorganotin compound and correspondingly 4 to 5% of the diorganotin compound. The individual compounds of the invention can also be a mixed mono-diorganotin compound as will be seen from some of the specific examples.

The compounds of the present invention can have the formula:

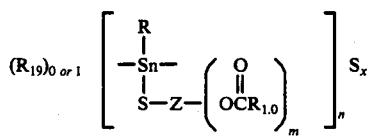

where R is hydrocarbyl, e.g., alkyl, aryl, cycloalkyl, aralkyl or alkenyl and R usually has 1 to 20 carbon atoms, $R_{19}$ is R or

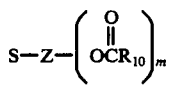

where Z is a polyvalent alkylene or hydroxyalkylene radical of at least 2 carbon atoms and usually not over 20 carbon atoms the valency of Z being $m+1$, $R_{10}$ is as defined below, $m$ is the number of $OOCR_{10}$ groups, $m$ is an integer of 1 to 3, $n$ is an integer from 1 to 2 and $x$ is 1 to 10, usually 1 to 4.

In a more specific form, the compounds of the invention can have the formula:

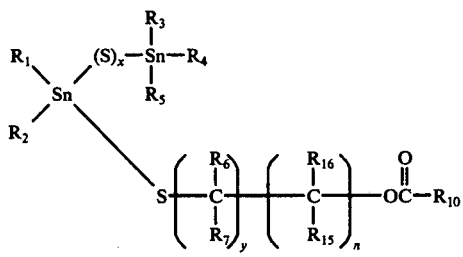

where $x$ is 1 to 10, usually 1 to 4 and preferably 1 to 3, most preferably 1 to 2, $y$ is at least 1, $Z$ is 0 or an integer and $y+z$ is at least 2 and can be as high as 18 or 20 or higher, $R_1$, $R_2$, $R_3$, $R_4$ and $R_9$ are hydrocarbyl, e.g., alkyl, aryl, cycloalkyl, aralkyl or alkenyl having 1 to 20 carbon atoms,

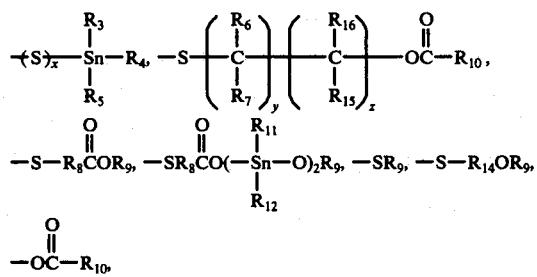

halogen, e.g., Cl, Br or I or OH, $R_5$ is as defined for $R_1$, $R_2$, $R_3$ and $R_4$ but is preferably not hydrocarbyl since the presence of a trihydrocarbyltin group tends to decrease the effectiveness and to increase the toxicity of the compound, $R_6$ and $R_{16}$ are hydrogen, hydroxyl,

alkyl, e.g., of 1 to 18 carbon atoms, $R_7$ and $R_{15}$ are hydrogen or alkyl, e.g., of 1 to 18 carbon atoms, $R_{10}$ is hydrogen, alkyl, aryl, aralkyl, cycloalkyl, aralkenyl, alkenyl having up to 3 ethylenic double bonds, hydroxy-alkyl, hydroxyalkenyl or -$R_{14}COOR_{23}$, where $R_{14}$ is $(CH_2)_p$, phenylene or —CH=CH— where $p$ is 0 or an integer up to 8 and $R_{23}$ is alkyl of 1 to 20 carbon atoms, cycloalkyl of 5 to 6 carbon atoms, alkenyl of 2 to 20 carbon atoms, aryl, e.g., phenyl or tolyl or benzyl. $R_{10}$ can have 1 to 19 carbon atoms or more when it is a hydrocarbon or hydroxy-hydrocarbon group. Preferably it has 7 to 17 carbon atoms. $R_8$ is alkylene (including alkylidene) of 1 to 20 carbon atoms or such an alkylene having a halo or hydroxy substituent, or ethylenically unsaturated divalent aliphatic hydrocarbon or hydroxy hydrocarbon group having 2 to 19 carbon atoms, $R_{11}$ and $R_{12}$ are hydrocarbyl, e.g., alkyl, aryl, cycloalkyl, aralkyl or alkenyl having 1 to 20 carbon atoms, $R_{14}$ is alkylene of 2 to 20 carbon atoms. At least one of $R_1$, $R_2$, $R_3$ and $R_4$ must be hydrocarbyl and preferably at least one of $R_3$ and $R_4$ is hydrocarbyl.

In addition to the group of compounds set forth above, there can also be employed overbased tin compounds by reacting a compound of the formula:

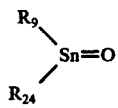

where $R_{24}$ is defined as $R_9$ in an amount of up to 2 moles per available carboxyl group with a tin sulfide of the invention. The "overbased" product can be obtained simply by dissolving the dihydrocarbyltin oxide in the tin mercaptoalkyl carboxylic acid ester sulfide, for example. The overbased product has the same uses as the other products of the invention. It is particularly surprising that overbased products can be made with dimethyltin oxide since while it is not soluble in other materials, it is soluble in the compounds of the invention.

The overbasing reaction is further shown in Weisfeld, U.S. Pat. No. 3,478,071 and Stapfer et al, J. Organometallic Chemistry Vol. 24 (1970) pages 355–358. The entire disclosures of the Weisfeld patent and Stapfer article are hereby incorporated by reference.

As employed in the claims, the term overbased with dihydrocarbyltin oxide (or

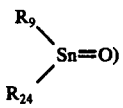

means the reaction product of such organotin oxide with a mono or diorganotin mercaptoalkyl (or mercapto-hydroxyalkyl carboxylic acid ester sulfide). While not being limited to any theory, it is believed that the overbasing reaction proceeds in the following manner:

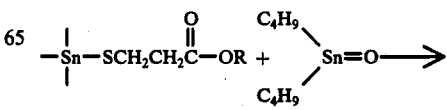

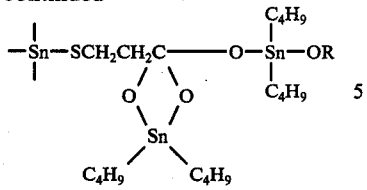

In preparing the compounds of the present invention when the $R_1$, $R_2$, $R_3$, $R_4$ and $R_5$ groups attached to tin are hydrocarbyl they can be, for example, methyl, ethyl, propyl, isopropyl, n-butyl, isobutyl, sec. butyl, t-butyl, amyl, hexyl, octyl, isooctyl, 2-ethylhexyl, benzyl, phenyl, p-tolyl, dodecyl, allyl, eicosanyl, benzyl, phenyl, p-tolyl, dodecyl, allyl, eicosanyl, octadecyl, oleyl, vinyl, cyclopentyl or cyclohexyl.

The compounds of the present invention can be made in various ways such as those illustrated below, for example. Thus, there can be used the procedure of Kauder, U.S. Pat. No. 3,565,930 or Brecker, U.S. Pat. No. 3,565,931 substituting alkali metal, alkaline earth metal or ammonium sulfides or polysulfides, e.g., $Na_2S_x$, $K_2S_x$, $CaS_x$, $BaS_x$ or $(NH_4)_2S_x$ where x is as defined above for the alkali metal or alkaline earth metal monosulfide of Kauder or Brecker and also substituting a compound having the formula:

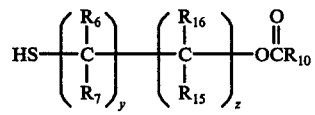

for the isooctyl thioglycolate or the like in Brecker or Kauder. In the event that one or more of the $R_1$, $R_2$, $R_3$, $R_4$ and $R_5$ groups are:

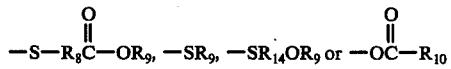

there is also present a compound of the formula

Thus, there can be reacted 1 mol of a compound of the formula

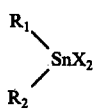

with 1 mole of a compound having the formula:

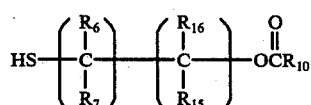

followed by neutralization with an alkali or alkaline earth metal hydroxide in an amount equal to the mercaptoalkanol ester of the carboxylic acid followed by reaction with ammonium or an alkali or alkaline earth metal sulfide. If the compound

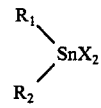

is replaced by a compound having the formula $R_1\text{-}SnX_3$, then there should be employed 2 mols of the mercaptoalkanol ester. X can be a halogen of atomic weight 35 to 127. Thus as starting material there can be used methyltin trichloride, methyltin tribromide, methyltin triiodide, ethyltin trichloride, butyltin trichloride, butyltin tribromide, butyltin triiodide, sec. butyltin trichloride, octyltin trichloride, benzyltin trichloride, dimethyltin dichloride, dimethyltin dibromide dimethyltin diiodide, dipropyltin dichloride, butyl methyl tin dichloride, dibutyltin dichloride, dibutyltin dibromide, dioctyltin diiodide, dioctyltin dichloride, dibenzyltin dichloride, phenyltin trichloride, p-tolyltin trichloride, diphenyltin dichloride, di-p-tolyltin dichloride, cyclohexyltin trichloride, dicyclohexyltin dichloride, cyclopentyltin trichloride, oleyltin trichloride, dioleyltin dichloride, vinyltin trichloride, diallyltin dichloride, allyltin trichloride, eicosanyltin trichloride.

As the mercaptoalkanol ester there can be employed, for example, esters of mercaptoethanol, 2-thioglycerine, 3-thioglycerine, 3-thiopropanol, 2-thiopropanol, 4-thiobutanol, 18-thiooctadecanol, 9-thiononanol, 8-thiooctanol, 6-thiohexanol with acids such as formic acid, acetic acid, propionic acid, butyric acid, pivalic acid, valeric acid, caprylic acid, caproic acid, decanoic acid, lauric acid, myristic acid, palmitic acid, 2-ethylhexanoic acid, stearic acid, eicosanic acid, oleic acid, linoleic acid, linolenic acid, crotonic acid, methacrylic acid, acrylic acid, cinnamic acid, benzoic acid, p-toluic acid, o-toluic acid, p-t-butylbenzoic acid, enanthic acid, p-n-butylbenzoic acid, cyclohexane carboxylic acid, phenylacetic acid, ricinoleic acid, hydrogenated ricinoleic acid, phenylpropionic acid. Of course, mixtures of acids can be used, e.g., tall oil acids, palmitic acid-stearic acid mixtures ranging from 60:40 to 40:60, soybean oil acids, cottonseed oil acids, hydrogenated cottonseed oil acids, peanut oil acids, coconut oil acids, corn oil acids, castor oil acids, hydrogenated castor oil acids, lard acids, etc. Illustrative of half esters of polycarboxylic acids which can be esterified with the mercaptoalkanol are monomethyl maleate, monoethyl maleate, monopropyl maleate, monobutyl maleate, monooctyl maleate, mono-2-ethylhexyl maleate, monostearyl maleate, monoethyl fumarate, mono methyl oxalate, monoethyl oxalate, monoethyl malonate, monobutyl malonate, monoisopropyl succinate, monomethyl succinate, monomethyl glutarate, monoethyl adipate, monomethyl azelate, monomethyl phthalate, monoethyl phthalate, monoisooctyl phthalate, monoethyl terephthalate.

Illustrative of mercapto esters which can be used for reaction with the tin compound are:

2-mercaptoethyl acetate,
2-mercaptoethyl propionate,
2-mercaptoethyl butyrate,
2-mercaptoethyl valerate,
2-mercaptoethyl pivalate,
2-mercaptoethyl caproate,
2-mercaptoethyl caprylate,
2-mercaptoethyl pelargonate,
2-mercaptoethyl decanoate, 2-mercaptoethyl laurate,
2-mercaptoethyl stearate,
2-mercaptoethyl eicosanate,
2-mercaptoethyl palmitate,
2-mercaptoethyl oleate,
2-mercaptoethyl ricinoleate,
2-mercaptoethyl linoleate,
2-mercaptoethyl linolenate,
2-mercaptoethyl tallate,
2-mercaptoethyl ester of cottonseed oil acid,
2-mercaptoethyl ester of lard acids,
2-mercaptoethyl ester of coconut oil acids,
2-mercaptoethyl ester of soybean oil acids,
2-mercaptoethyl benzoate,
2-mercaptoethyl p-toluate,
2-mercaptoethyl crotonate,
2-mercaptoethyl cinnamate,
2-mercaptoethyl phenyl acetate,
2-mercaptoethyl phenyl propionate,
2-mercaptoethyl methyl maleate,
2-mercaptoethyl ethyl fumarate,
2-mercaptoethyl butyl oxalate,
2-mercaptoethyl methyl oxalate,
2-mercaptoethyl ethyl malonate,
2-mercaptoethyl methyl succinate,
2-mercaptoethyl methyl azelate,
2-mercaptoethyl hexyl azelate,
2-mercaptoethyl methyl phthalate,
3-mercaptopropyl pelargonate,
3-mercaptopropyl enanthate,
3-mercaptopropyl stearate,
3-mercaptopropyl oleate,
3-mercaptopropyl ricinoleate,
3-mercaptopropyl ethyl maleate,
3-mercaptopropyl benzoate,
2-thioglyceryl pelargonate,
3-thioglyceryl pelargonate,
6-mercaptohexyl acetate,
7-mercaptoheptyl acetate,
7-mercaptoheptyl propionate,
8-mercaptooctyl acetate,
8-mercaptooctyl enanthate,
18-mercaptooctadecyl acetate,
18-mercaptooctadecyl enanthate.

When there is also present a compound of the formula

there can be used, for example, esters of mercaptoacetic acid, alpha mercaptopropionic acid, beta mercaptopropionic acid, alpha mercaptobutyric acid, beta mercaptobutyric acid, gamma mercaptobutyric acid, gamma mercapto valeric acid, alpha mercapto valeric acid, beta mercapto valeric acid. Thus, there can be used methyl mercaptoacetate (methyl thioglycolate), ethyl mercaptoacetate, propyl mercaptoacetate, butyl mercaptoacetate, isobutyl mercaptoacetate, sec. butyl mercaptoacetate, t-butyl mercaptoacetate, amyl mercaptoacetate, hexyl mercaptoacetate, octyl mercaptoacetate, isooctyl mercaptoacetate, 2-ethylhexyl mercaptoacetate, decyl mercaptoacetate, isodecyl mercaptoacetate, lauryl mercaptoacetate, myristyl mercaptoacetate, hexadecyl mercaptoacetate, stearyl mercaptoacetate, allyl mercaptoacetate, methallyl mercaptoacetate, crotyl mercaptoacetate, oleyl mercaptoacetate, cyclopentyl mercaptoacetate, cyclohexyl mercaptoacetate, 2-methylcyclohexyl mercaptoacetate, benzyl mercaptoacetate, methyl beta mercaptopropionate, ethyl beta mercaptopropionate, isopropyl beta mercaptopropionate, octyl beta mercaptopropionate, isooctyl beta mercaptopropionate, 2-ethylhexyl beta mercaptopropionate, decyl beta mercaptopropionate, octadecyl beta mercaptopropionate, allyl beta mercaptopropionate, oleyl beta mercaptopropionate, benzyl beta mercaptopropionate, cyclohexyl beta mercaptopropionate, methyl alpha mercaptopropionate, hexyl alpha mercaptopropionate, nonyl alpha mercaptopropionate, octyl alpha mercaptopropionate, isooctyl alpha mercaptopropionate, stearyl alpha mercaptopropionate, oleyl alpha mercaptopropionate, methyl alpha mercaptobutyrate, octyl alpha mercaptobutyrate, isooctyl alpha mercaptobutyrate, octadecyl alpha mercaptobutyrate, oleyl alpha mercaptobutyrate, ethyl gamma mercaptobutyrate, octyl gamma mercapto butyrate, 2-ethylhexyl gamma mercaptobutyrate, isooctyl gamma mercaptobutyrate, benzyl gamma mercaptobutyrate, cyclopentyl gamma mercaptobutyrate, oleyl gamma mercaptobutyrate, isopropyl delta mercaptovalerate, octyl delta mercaptovalerate, isooctyl delta mercaptovalerate, octadecyl delta mercaptovalerate, oleyl delta mercaptovalerate, cyclohexyl delta mercaptovalerate and benzyl delta mercaptovalerate, methyl mercaptan, ethyl mercaptan, butyl mercaptan, octyl mercaptan, dodecyl mercaptan, stearyl mercaptan, oleyl mercaptan, methoxy ethyl mercaptan, ethoxyethyl mercaptan, octoxyethyl mercaptan, ethoxypropyl mercaptan, acetic acid, stearic acid, benzoic acid, caproic acid, caprylic acid, decanoic acid, enanthic acid, oleic acid.

In preparing the compounds of the invention, numerous processes can be employed as set forth hereinafter. Regardless, however, of the method employed, the reaction can be carried out at a wide range of temperatures, e.g., room temperature to 100° C. usually at 25°–50° C. The reaction is usually carried out with water as a solvent, regardless of the procedure employed. There can also be employed water immiscible organic solvents, e.g., aliphatic and aromatic hydrocarbons, e.g., hexane, octane, benzene, toluene, xylene, aliphatic carboxylic acid esters, e.g., butyl acetate, propyl propionate, methyl valerate. The proportions of solvent are not critical and can vary widely.

Unless otherwise indicated, all parts and percentages are by weight.

In the examples the refractive indices (R.I.) were measured at 25° C. unless otherwise indicated. Illustrative procedures include:

PROCEDURE 1

This follows the general procedure of Kauder and Brecker except that sodium monosulfide, sodium disulfide, sodium trisulfide, sodium tetrasulfide, ammonium monosulfide, ammonium disulfide, ammonium trisulfide or ammonium tetrasulfide is reacted with the appropriate tin compound and appropriate —SH containing compound or compounds as indicated above, for example.

PROCEDURE 2

In this procedure, the sodium mono or polysulfide (or potassium mono or polysulfide), water, mercapto containing ester, hydrocarbon if desired and ammonium hydroxide are charged into a reactor and an aqueous solution of an alkyltin halide slowly added, e.g., at 25°–35° C. The mixture is then heated, e.g., to 50° C., the layers separated, and the product is wahsed and dried.

PROCEDURE 3

In this method the mercapto containing ester, water, organic solvent and ammonium hydroxide are charged into a flask and then two solutions (A) alkyltin chloride and (B) alkali metal mono or polysulfide are added simultaneously. The product is then separated, washed and stripped.

PROCEDURE 4

This is the same procedure as Procedure 3 except that NaHCO$_3$ is substituted in the same molar amount for the ammonium hydroxide.

PROCEDURE 5

In this procedure the alkyltin chloride, water and ammonium hydroxide are charged into a flask and then there are added simultaneously the mercapto containing ester and alkali metal mono or polysulfide.

PROCEDURE 6

This method comprises charging the mercapto containing ester, water and ammonium hydroxide into a reactor and then adding an alkyltin chloride followed by an alkali metal polysulfide or monosulfide slowly at 30° C. After heating to 45° C. the product was separated, washed and stripped.

These basic procedures are described in further detail in Kugele et al application Ser. No. 400,127 filed Sept. 24, 1973. The entire disclosure of Kugele et al is hereby incorporated by reference. The working examples of Kugele et al can be followed replacing in whole or in part the mercapto compounds employed by Kugele with the mercapto compounds of the formula:

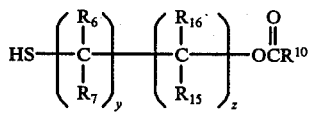

The stabilizers of the present invention can be used with halogen containing vinyl and vinylidene polymers, e.g., resins in which the halogen is attached directly to the carbon atoms. Preferably the polymer is a vinyl halide polymer, specifically a vinyl chloride polymer. Usually, the vinyl chloride polymer is made from monomers consisting of vinyl chloride alone or a mixture of monomers comprising at least 70% vinyl chloride by weight. When vinyl chloride copolymers are stabilized, preferably the copolymer of vinyl chloride with an ethylenically unsaturated compound copolymerizable therewith contains at least 10% of polymerized vinyl chloride.

As the chlorinated polymer there can be employed chlorinated polyethylene having 14 to 75%, e.g., 27% chloride by weight, chlorinated natural and synthetic rubber, rubber hydrochloride, chlorinated polystyrene, chlorinated polyvinyl chloride, polyvinyl chloride, polyvinylidene chloride, polyvinyl bromide, polyvinyl fluoride, copolymers of vinyl chloride with 1 to 90%, preferably 1 to 30% of a copolymerizable ethylenically unsaturated material such as vinyl acetate, vinyl butyrate, vinyl benzoate, vinylidene chloride, diethyl fumarate, diethyl maleate, other alkyl fumarates and maleates, vinyl propionate, methyl acrylate, 2-ethylhexyl acrylate, butyl acrylate and other alkyl acrylates, methyl methacrylate, ethyl methacrylate, butyl methacrylate and other alkyl methacrylates, methyl alpha chloroacrylate, styrene, trichloroethylene, vinyl ethers such as vinyl ethyl ether, vinyl chloroethyl ether and vinyl phenyl ether, vinyl ketones such as vinyl methyl ketone and vinyl phenyl ketone, 1-fluoro-2-chloro-ethylene, acrylonitrile, chloroacrylonitrile, allylidene diacetate and chloroallylidene diacetate. Typical copolymers include vinyl chloride-vinyl acetate (96:4 sold commercially as VYNW), vinyl chloride-vinylacetate (87:13), vinyl chloride-vinyl acetate-maleic anhydride (86:13:1), vinyl chloride-vinylidene chloride (95:5), vinyl chloride-diethyl fumarate (95:5), vinyl chloride-trichloroethylene (95:5), vinyl chloride-2-ethylhexyl acrylate (80:20).

The stabilizers of the present invention can be incorporated with the polymer by admixing in an appropriate mill or mixer or by any of the other well-known methods which provide for uniform distribution throughout the polymer composition. Thus, mixing can be accomplished by milling on rolls at 100°–160° C.

In addition to the novel stabilizers, there can also be incorporated with the resin, conventional additives such as plasticizers, pigments, fillers, dyes, ultraviolet light absorbing agents, densifying agents and the like. There can also be added conventional and known tin stabilizers, e.g., those disclosed in Kauder or Kugele et al or in Weisfeld U.S. Pat. No. 3,640,950, Leistner, U.S. Pat. Nos. 2,870,119 and 2,870,182, Best, U.S. Pat. No. 2,731,484, Stefl U.S. Pat. No. 2,731,482, and Mack, U.S. Pat. No. 2,914,506, for example. The entire disclosures of all the patents mentioned in this paragraph are herby incorporated by reference.

If the plasticizer is employed, it is used in conventional amount, e.g., 10 to 150 parts per 100 parts of polymer. Typical plasticizers are di-2-ethylhexyl phthalate, dibutyl sebacate, dioctyl sebacate, tricresyl phosphate.

The tin containing stabilizers of the invention are normally used in an amount of 0.01 to 10% by weight of the polymer, more preferably 0.2 to 5% of the tin compound is used by weight of the polymer.

As indicated, there can also be incorporated 0.1 to 10 parts per 100 parts of the halogen containing polymer of a metal salt stabilizer. Thus, there can be used barium, strontium, calcium, cadmium, zinc, lead, tin, magnesium, cobalt, nickel, titanium and aluminum salts of phenols, aromatic carboxylic acids, fatty acids or epoxy fatty acids.

Examples of suitable salts include barium di(nonylphenolate), strontium di(nonylphenolate), strontium di(amylphenolate), barium di(octylphenolate), strontium di(octylphenolate), barium di(nonyl-o-cresolate), lead di(octylphenolate), cadmium-2-ethyl-hexoate, cadmium laurate, cadmium stearate, zinc caprylate, cadmium caprate, barium stearate, barium-2-ethylhexoate, barium laurate, barium ricinoleate, lead stearate, aluminum stearate, magnesium stearate, calcium octoate, calcium stearate, cadmium naphthenate, cadmium benzoate, cadmium p-tert. butylbenzoate, barium octyl salicylate, cadmium epoxy stearate, strontium epoxy stearate, cadmium salt of epoxidized acids of soybean oil, and lead epoxy stearate.

In plastisol formulations there is preferably also included from 0.1 to 10 parts per 100 parts of polymer of an expoxy vegetable oil such as epoxidized soybean oil or epoxidized tall oil, epoxy esters of fatty acids, e.g., isooctyl epoxystearate.

In the following examples there are included mention of monoalkyltin tris(mercaptoalkanyl) alkanoates and dialkyltin bis(mercaptoalkanyl)alkanoates and the like because, although they are not within the present invention, their use in admixture with the compounds of the invention is within the invention. The mono and polysulfides of the invention can also be formed by reacting ammonium and/or alkali metal mono or polysulfide with such mono and dialkyltin mercapto alkanyl alkanoates.

EXAMPLE 1

Into a 2 liter flask is placed 204 gm (1.0 mole) 2-mercapto-ethylcaprylate, 200 ml water, 84 gm (1.0 mole) sodium bicarbonate and 300 ml heptane. To the above stirred mixture is added dropwise, at 30°-40° C., 110 gms (0.5 mole) dimethyltin dichloride dissolved in 200 ml water. Stir for 1 hour at 30°-40° C. and allow the layers to separate. The organic layer is washed with 200 ml water and then stripped under vacuum at about 100° C. A yield of 273 gm of dimethyltin bis(2-mercaptoethyl caprylate) is obtained. $n_D^{25}$ 1.5060.

EXAMPLE 2

Into a 2 liter flask is placed 306 gm (1.5 mole) of 2-mercaptoethyl caprylate, 200 ml water, 126 gm (1.5 mole) sodium bicarbonate and 300 ml heptane. To the above stirred mixture is added, at 40° C, 120 gm (0.5 mole) monomethyltin trichloride dissolved in 150 ml water. When addition is complete, allow to stir 1 hour at 30°-40° C. The layers are separated and the organic phase is washed with 200 ml water. The heptane is then remowved under vacuum. A yield of 363 gm monomethyltin tris(2-mercapto-ethylcaprylate) is obtained as a clear colorless liquid. $n_D^{25}$ 1.5041.

EXAMPLE 3

Into a 2 liter flask is placed 516 (1.5 mole) of 2-mercaptoethyl stearate, 200 ml water, 126 gm sodium bicarbonate and 500 ml heptane. To the above stirred mixture is added, at 40°-50° C, 120 gm (0.5 mole) monomethyltin trichloride dissolved in 150 ml water. When addition is complete stir 1 hour at 40°-50° C, then allow the layers to separate. The organic phase is washed with 200 ml water and then stripped under vacuum at about 100° C. A yield of 560 gm monomethyltin tris(2-mercapto-ethyl stearate) is obtained as a white solid, m.p. 44°-47° C.

EXAMPLE 4

Into a 2 liter flask is placed 430 gm (1.25 mole) 2-mercaptoethyl stearate, 200 ml water, 69 (0.65 mole) sodium carbonate and 300 ml heptane. To the above stirred mixture is added, at 30°-40° C, 55 gm (0.25 mole) dimethyltin dichloride and 60 gm (0.25 mole) monomethyltin trichloride dissolved in 150 ml of water. When addition is complete, stir 1 hour at reaction temperature then allow to separate. The organic phase is washed with 200 ml water and then stripped under vacuum at about 100° C, yielding 493 gm of a colorless oil. The product is a mixture of monomethyl-dimethyltin tris,-bis(2-mercaptoethyl stearate). M.P. 36°-40° C.

EXAMPLE 5

Into a 2 liter flask is placed 182 gm (1.5 mole) 2-mercaptoethyl acetate, 200 ml water, 300 ml heptane and 120 gm (0.5 mole) monomethyltin trichloride. To the above stirred mixture is added portionwise 126 gm (1.5 mole) sodium bicarbonate maintaining a pot temperature of 25°-40° C. by the addition rate. When addition is complete, allow to stir 1 hour at 25°-40° C. The layers are separated and the organic phase washed with 200 ml water. The heptane is removed under vacuum. A yield of 240 gm, monomethyltin tris(2-mercaptoethyl acetate) is obtained as a colorless oil. $n_D^{25}$ 1.5575.

EXAMPLE 6

Into a 2 liter flask is placed 513 gm (1.5 mole) 2-mercapto ethyl oleate, 200 ml water, 126 gm sodium bicarbonate, and 500 ml heptane. To the above stirred mixture is added, at 25°-35° C, 120 gm (0.5 mole) monomethyltin trichloride dissolved in 150 ml water. When addition is completed, stir 1 hour at 25°-35° C, then allow layers to separate. The organic layer is washed with 200 ml water and then stripped under vacuum at 100° C. Monomethyltin tric(2-mercaptoethyl oleate) is obtained in 98.5% yield as a pale yellow oil. $n_D^{25}$ 1.5008.

EXAMPLE 7

The procedure of Example 2 was repeated, substituting 142 gm (0.50 mole) monobutyltin trichloride for the monomethyltin trichloride. The yield is 383 gm colorless oil consisting of monobutyltin tris(2-mercaptoethyl caprylate). $n_D^{25}$ 1.5061.

EXAMPLE 8

The procedure of Example 1 was repeated, substituting 52 gm (0.125 mole) dioctyltin dichloride and 85 gm (0.25 mole) monooctyltin trichloride for the dimethyltin dichloride. The yield is 297 gm of a pale yellow oil consisting of dioctyltin bis(2-mercaptoethyl caprylate) and monooctyltin tris(2mercapto-ethylcaprylate). $n_D^{25}$ 1.5001.

EXAMPLE 9

Into a 2 liter flask is placed 204 gm (1.0 mole) of a 2-mercaptoethyl caprylate, 200 ml water, 300 ml heptane and 120 gm (0.5 mole) monomethyltin trichloride. To the above stirred mixture is added 80 gms (1.0 mole) 50% aqueous NaOH solution at a temperature of 25°-35° C. Allow to stir 1 hour under these conditions whence the layers are separated and the organic phase is stripped under reduced pressure yielding 273 gms of a pale yellow oil. The product consists mainly of monomethylmonochlorotin bis(2-mercaptoethyl caprylate). $n_D^{25}$ 1.5244.

EXAMPLE 10

Into a 2 liter flask is placed 286 gm (1.5 mole) monothioglycerine diacetate ester, 200 ml water, 126 gm sodium bicarbonate and 500 ml heptane. To the above stirred mixture is added, at 40°-50° C., 120 gm (0.5 mole) monomethyltin trichloride dissolved in 150 ml water. When addition complete, stir 1 hour at 40° C. then allow the layers to separate. The organic phase is washed with 200 ml water and then stripped under vacuum at about 100° C. A yield of 328 gm, consisting mainly of monomethyltin tris (monothioglycerine diacetate) as a thick oil is obtained. $n_D^{25}$ 1.5310.

EXAMPLE 11

Into a 2 liter flask is placed 120 gm (0.5 mole) monomethyltin trichloride dissolved in 200 ml of water. Warmed to 30° C. and added 204 gm (1.0 mole) 2-mercaptoethyl caprylate. Then added dropwise at 30°-40° C. 80 gm (1.0 mole) 50% aqueous sodium hydroxide solution. The mixture is stirred for 1 hour. After this addition, a solution formed by heating 32.5 gm (0.25 mole) 60% aqueous Na$_2$S and 8.0 gm (0.25 mole) sulfur in 100 ml of water was added dropwise at 25°-35° C. After stirring for 1 hour at 35° C. the product layer was separated and washed with 200 ml of water. The product was then stripped to 100° C. under vacuum resulting in a 100% yield of a pale yellow oil. The product is mainly bis(methyltin di-2-mercaptoethyl caprylate) disulfide. $n_D^{25}$ 1.5279.

EXAMPLE 12

The procedure of Example 11 was repeated, substituting 32.5 gm (0.25 mole) 60% aqueous sodium sulfide in place of the formed (0.25 mole) sodium disulfide to form the corresponding monosulfide. Yield is 277 gm pale yellow oil. $n_D^{25}$ 1.5269.

EXAMPLE 13

The procedure of Example 11 was repeated substituting 96 gm (0.4 mole) methyltin trichloride, 33 gm (0.15 mole) dimethyltin dichloride for the 0.5 mole methyltin trichloride. Yield is 285 gm of pale yellow oil and consists mainly of [monomethyltin di(2-mercaptoethylcaprylate)][dimethyltin mono(2-mercaptoethyl caprylate)]disulfide. $n_D^{25}$ 1.5258.

EXAMPLE 14

To 120 gm (0.50 mole) monomethyltin trichloride in 200 ml of water warmed to 30° C. is added 204 gm (1.00 mole) of 2-mercaptoethyl caprylate, after which there was slowly added 31 gm (0.50 mole) 28% ammonium hydroxide. The mixture was stirred for 1 hour. Then there was added 125 gm (0.25 mole) of 20% aqueous ammonium disulfide solution over a 30 minute period at 25°-35° C. The mixture heated to 50° C. and the lower product layer separated from the aqueous phase. The product was washed with 200 ml of water and dried to 100° C. at 2 mm Hg pressure absolute. A quantative yield of a pale yellow oil is obtained. The yield is mainly bis[monomethyltin bis(2-mercaptoethyl caprylate)]disulfide. $n_D^{25}$ 1.5288.

EXAMPLE 15

Into a 2 liter flask was charged 32.5 gm (0.25 mole) 60% aqueous sodium sulfide and 8.0 gm (0.25 mole) sulfur dissolved in 100 ml of water, 300 ml of heptane, 150 ml of water, 218 gm (1.0 mole) 2-mercaptoethyl pelargonate and 61 gm (1.0 mole) 28% aqueous ammonium hydroxide. Then there was added a mixture of 96 gm (0.4 mole) methyltin trichloride and 33 gm (0.15 mole) dimethyltin dichloride dissolved in 150 ml of water. Then the mixture was heated to 50° C. for 30 minutes, the layers separated, and the product layer washed and dried to 100° C. under vacuum. The product (99%) consisted mainly of bis[methyl/dimethyltin mono/di(2-mercaptoethyl pelargonate)]disulfide. $n_D^{25}$ 1.5245.

EXAMPLE 16

The procedure of Example 15 was repeated, substituting 32.5 gm (0.25 mole) 60% aqueous sodium sulfide in place of the formed sodium disulfide to form the corresponding monosulfide. yield 296 gm of a pale yellow oil. $n_D^{25}$ 1.5222.

EXAMPLE 17

Into a 2 liter flask is placed 300 ml of heptane, 91 gm (1.5 moles) 28% aqueous ammonium hydroxide, 200 ml of water and 218 gm (1.0 mole) 2-mercaptoethyl pelargonate. Then there is added a mixture of 120 gm (0.50 mole) methyltin trichloride dissolved in 150 ml of water. The mixture is heated to 35° C, held for 30 minutes, the layers separated, the product layer washed and dried at 100° C. under reduced pressure. The product (206 gm) contained bis[monomethyltin bis(2-mercaptoethyl pelargonate)]oxide. $n_D^{25}$ 1.5197.

EXAMPLE 18

Into a 2 liter flask is placed 120 gm (0.5 mole) methyltin trichloride dissolved in 200 ml of water. The mixture is warmed to 30° C. and 163.5 gm (0.75 mole) 2-mercaptoethyl pelargonate added. Then there is added dripwise, at 30-40° C., 60 gm (0.75 mole) 50% aqueous sodium hydroxide solution. The mixture is stirred for 1 hour. After this addition, a solution formed by heating 32.5 gm (0.25 mole) 60% aqueous Na$_2$S. 100 ml of water was added portionwise at 25°-35° C., stirred for 1 hour after addition completed, then separated layers, washed product layer with 200 ml of water. The organic layer was stripped to 100° C under vacuum resulting in 240 gm pale yellow oil containing [monomethylmonochlorotin 2-mercaptoethyl pelargonate][monomethyltin bis(2-mercaptoethyl pelargonate)]sulfide. $n_D^{25}$ 1.5293.

EXAMPLE 19

Into a 2 liter flask is placed 120 gm (0.5 mole) methyltin trichloride in 200 ml of water. Warmed to 30° C. and added 153 gm (0.75 mole) 2-mercaptoethyl caprylate and 50.5 gm (0.25 mole) lauryl mercaptan. Then added dropwise, at 30°-40° C. 61 gm (1.0 mole) 28% aqueous ammonium hydroxide. The mixture is stirred for 1 hour. After this time, a solution of 32.5 gm (0.25 mole) 60% aqueous sodium sulfide in 100 ml water was added dropwise at 35° C. Stirred for 1 hour after addition complete, separated layers and washed organic layer with 200 ml water. The organic phase was stripped to 100° C. under vacuum resulting in 269 gm yellow oil containing mainly [monomethyltin bis(2-mercaptoethyl caprylate)][monomethyltin mono(2-mercaptoethyl caprylate) monolauryl mercaptide] sulfide. $n_D^{25}$ 1.5267.

EXAMPLE 20

The procedure of Example 19 was repeated, substituting 51 gm (0.25 mole) isooctylthioglycolate for the lauryl mercaptide. The yield was 272 gm pale yellow oil, [monomethyltin bis(2-mercaptoethyl caprylate)][monomethyltin mono(2-mercaptoethyl caprylate)monoisooctylthioglycolate]sulfide. $n_D^{25}$ 1.5278.

EXAMPLE 21

The procedure for Example 19 was repeated, substituting 54.5 (0.25 mole) isooctylmercaptopropionate and 0.25 mole sodium disulfide for the lauryl mercaptan and sodium sulfide, respectively. The yellow oil, consisting mostly of [monomethyltin bis(2-mercaptoethyl caprylate)][monomethyltin mono(2-mercaptoethyl caprylate) monoisooctyl mercaptopropionate]disulfide weighed 274 gm. $n_D^{25}$ 1.5266.

EXAMPLE 22

The procedure of Example 19 was repeated, substituting 36 gm (0.25 mole) 2-ethylhexoic acid for the lauryl mercaptan. The yield was 251 gm yellow oil containing [monomethyltin bis(2-mercaptoethyl caprylate)][monomethyltin mono(2-mercaptoethyl caprylate)mono(2-ethylhexoate)]sulfide. $n_D^{25}$ 1.5214.

EXAMPLE 23

The procedure of Example 15 was repeated, substituting 258 (0.75 mole) 2-mercaptoethyl stearate and 57 (0.25 mole) isooctyl maleate for the (1.0 mole) 2-mercaptoethyl pelargonate. A low melting white solid, 38°–43° C., (370 gm) is obtained consisting mostly of [monomethyltin bis(2-mercaptoethyl stearate)][monomethyltin mono(2-mercaptoethyl stearate)-monoisooctyl maleate]disulfide. $n_D^{25}$ 1.5193.

EXAMPLE 24

Into a 2 liter flask is placed 204 gm (1.0 mole) 2-mercaptoethyl caprylate, 102 gm (0.5 mole) isooctylthioglycolate, 200 ml water, 300 ml of heptane and 126 gm (1.5 mole) sodium bicarbonate. To the above stirred solution is added dropwise, at 25°–30° C., a solution of 120 gm (0.5 mole) methyltin trichloride in 150 ml water. When addition is complete, stir 1 hour at 40° C. then allow the layers to separate. The organic phase is washed with 200 ml of water and then stripped under vacuum to 100° C. A yield of 366 gm consisting mainly of monomethyltin bis(2-mercaptoethyl caprylate) monoisooctylthioglycolate is obtained as a pale yellow oil. $n_D^{25}$ 1.5103.

EXAMPLE 25

Into a 2 liter flask is placed 120 gm (0.5 mole) monomethyltin trichloride dissolved in 200 ml of water. Warmed to 30° C and added dropwise at 30-40° C. 80 gm (1.0 mole) 50% aqueous sodium hydroxide solution. The mixture is stirred for 1 hour. After this addition, a solution of 32.5 gm (0.25 mole) 60% aqueous sodium sulfide in 100 ml of water is added dropwise at 25°–35° C. After stirring for 1 hour at 35° C. the product layer is separated and washed with 200 ml of water. The product is then stripped to 100° C. under vacuum resulting in a 100% yield of a yellow oil. The product is mainly bis[methyltin di(2-mercaptoethyl tallate)]sulfide. $n_D^{25}$ 1.5168.

EXAMPLE 26

Into a 2 liter flask is placed 785 gm (1.0 mole) methyltin tris(2-mercaptoethyl pelargonate) and 120 gm (0.5 mole) methyltin trichloride. The mixture is stirred at 50° C. for 1 hour. The resulting product, a clear and colorless oil (905 gms), is mainly monomethylmonochlorotin bis(2-mercaptoethyl pelargonate). $n_D^{25}$ 1.5248.

EXAMPLE 27

Into a 3-necked flask is placed 785 gms (1.0 mole) monomethyltin tris(2-mercaptoethyl pelargonate), 248 gms (1.0 mole) dibutyltin oxide and 750 ml of toluene. The mixture is stirred and heated at 100° C. for 2 hours during which time a clear solution is obtained. The solvent is removed under vacuum stripping yielding 1016 gms of a pale yellow oil. Monomethyltin bis(2-mercaptoethyl pelargonate)mono(2-mercaptoethyloxydibutyltin pelargonate) has a refractive index at 25° C. of 1. $n_D^{25}$ 1.5069.

EXAMPLE 28

Into a 2 liter flask is placed 120 gms (0.5 mole) monomethyltin trichloride dissolved in 200 ml of water. Warmed to 30° C. and added 197 gms (1.0 mole) 2-mercaptoethylphenyl acetate. Then added dropwise at 30°–40° C. 80 gm (1.0 mole) 50% aqueous sodium hydroxide. The mixture is stirred for 1 hour. After this reaction time, a solution of 32.5 gms (0.25 mole) of 60% sodium sulfide dissolved in 100 ml of water is added dropwise at 30°–35° C. After stirring for 1 hour the product layer is separated and washed with 200 ml of water. The product is then stripped under vacuum resulting in a 1–0% yield of a yellow oil. 270 gms of bis[monomethyltin bis(2-mercaptoethylphenyl acetate)] sulfide. $n_D^{25}$ 1.6122.

EXAMPLE 29

Into a 3-necked flask is placed 83 gm (0.5 mole) methylstannoic acid, 273 gm (1.5 mole) of 2-mercaptoethylbenzoate and 500 ml toluene. The mixture is refluxed for 3 hours, cooled to 30° C. and filtered. The organic layer is removed by vacuum stripping to 100° C. resulting in 322 gms of an off-white solid. The solid consists mostly of monomethyltin tris(2-mercaptoethyl) benzoate). M.P. 263°–267° C.

EXAMPLE 30

Into a 2 liter flask is placed 281 gm (1.0 mole) monobutyltin trichloride dissolved in 400 ml of water. Warmed to 30° C. and then added 436 gms (2.0 moles) of 2-mercaptoethyl pedargonate. Then added dropwise at 30°–35° C. 169 gm (2.0 moles) of 50% aqueous sodium hydroxide. The mixture is stirred for 1 hour. After this reaction time 65 gms (0.5 mole) of sodium sulfide (60%) dissolved in 100 ml of water is added dropwise at 40° C. After stirring 1 hour at this temperature the product layer is separated and washed with 400 ml of water. The product is then vacuum stripped to 100° C. resulting in 617 gms of a pale yellow oil, bis[monobutyltin bis(2-mercaptoethyl pelargonate)] sulfide. $n_D^{25}$ 1.5219.

EXAMPLE 31

Into a 2 liter flask is placed 281 gms (1.0 mole) butyltin trichloride dissolved in 400 ml of water. Warmed to 30° C. and added 101.5 gm (0.5 mole) of isooctylthioglyclate and 327 gm (1.5 moles) of 2-mercaptoethylpelargonate. Then added dropwise at 35°–40° C. 122 gms (2.0 moles) of ammonium hydroxide (28%). The mixture is stirred for 1 hour at 35°–40° C. After this reaction time 64 gms (0.50 mole) of ammonium sulfide (40%) is added and stirred 1 hour before the layers are separated. The product layer is washed with 400 ml water and dried under vacuum to 100° C. 596 gms of yellow oil, [monobutyltin bis(2-mercaptoethylpelargonate)] [monobutyltin(isooctylthioglycolate) (2-mercaptoethylpelargonate)] sulfide is obtained. $n_D^{25}$ 1.5211.

EXAMPLE 32

Into a 2 liter flask is placed 281 gm (1.0 mole) butyltin trichloride dissolved in 400 ml of water. Warmed to 30° C. and added 305 gms (1.5 moles) of 2-mercaptoethyl caprylate. Then added dropwise at 30°–40° C. 120 gms (1.5 moles of 50% aqueous sodium hydroxide, and stirred for 1 hour at this temperature. After this reaction time 65.0 gms (0.50 mole) of 60% Na₂S dissolved in 100 ml of water is added and stirred for 1 hour at 30°–40° C. The layers are separated and the product layer is washed with 400 ml of water, then stripped under vacuum to 100° C. The product [monobutylmonochlorotin(2-mercaptoethyl caprylate)] [monobutyltin bis(2-mercaptoethyl caprylate)]sulfide is obtained in 98% yield as a yellow oil. $n_D^{25}$ 1.5276.

EXAMPLE 33

Into a 2 liter flask is placed 240 gm (1.0 mole) monomethyltin trichloride dissolved in 400 ml of water. Warmed to 30° C. and added 218 gms (1.0 mole) of 2-mercaptoethyl pelargonate and 109 gms (0.5 mole) of isooctylmercaptopropionate. Then added dropwise 120 gm (1.5 moles) of 50% aqueous sodium hydroxide and stir for 1 hour at 25°–30° C. After this reaction time, 65.0 gm (0.50 mole) of 60% sodium sulfide dissolved in 100 ml of water is added and stirred for 1 hour at 30°–40° C. The layers are separated, the organic layer washed 400 of water and stripped under vacuum to 100° C. The product, 474 gms of a pale yellow oil, is mainly a mixture of [methyltin bis(2-mercaptoethylpelargonate)] [monomethylmonochlorotin(isooctylmercaptopropionate)] sulfide and [monomethyltin(isooctylmercaptopropionate) (2-mercaptoethyl pelargonate)] [monomethylmonochlorotin(2-mercaptoethyl pelargonate)[sulfide. $n_D^{25}$ 1.5288.

EXAMPLE 34

Into a 2 liter flask is place 240 gms (1.0 mole) monomethyltin trichloride dissolved in 400 ml of water. Warmed to 30° C. and added 218 gm (1.0 mole) of 2-mercaptoethyl pelargonate. Then added dropwise 80 gms (1.0 mole) of 50% aqueous sodium hydroxide and stir for 1 hour at 25°–35° C. After this reaction time, 65 gm (0.50 mole) of 60% sodium sulfide dissolved in 150 ml of water is added and stirred for 1 hour at 35° C. The layers are separated, the organic phase washed with 400 ml of water and stripped under vacuum to 100° C. The product, bis[monomethyltin (2-mercaptoethylpelargonate)] bis sulfide is obtained in 96.5% yield as a pale yellow oil. $n_D^{25}$ 1.5630.

EXAMPLE 35

Into a 2 liter flask is placed 240 gm (1.0 mole) monomethyltin trichloride dissolved in 400 ml of water. Warmed to 35° C. and added 660 gms (2.0 moles) of 2-mercaptoethyl oleate. Then added dropwise at at 35° C. 160 gm (2.0 moles) of 50% aqueous sodium hydroxide. The mixture is stirred for 1 hour. After this reaction time, a solution of 65 gm (0.5 mole) of 60% sodium sulfide dissolved in 150 ml of water is added dropwise at 30°–35° C. After stirring 1 hour the product layer is separated and washed with 400 ml of water, then stripped to 100° C. under vacuum resulting in 788 gm of a pale amber oil. The product consisted mainly of bis[-monomethyltin bis(2-mercaptoethyloleate)]sulfide. $n_D^{25}$ 1.5118.

EXAMPLE 36

Into a 3-necked flask is placed 120 gm (0.5 mole) methyltin trichloride in 150 ml of water, 109 gm (0.5 mole) of 2-mercaptoethylpelargonate and 200 ml toluene. The mixture is heated to 30° C. and then is added dropwise 40 gm (0.5 mole) of 50% aqueous sodium hydroxide, maintained at 30° C. and then add portionwise 43 gm (0.33 mole) of 60% Na₂S dissolved in 75 ml of water. Allow to stir at 30°–40° C. for 1 hour after addition complete. The layers are separated and the organic phase stripped to 100° C. under vacuum to yield 190 gm of colorless oil. $n_D^{25}$ 1.5336. The structure is thought to be:

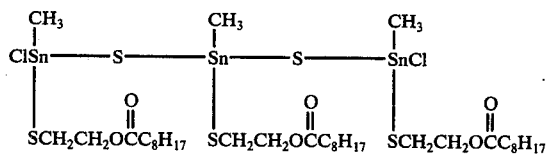

To 118.5 gm (0.1 mole) of the above is added 200 ml of water and 43.5 gms (0.2 mole) of 2-mercaptoethyl pelargonate. Then is added dropwise at 25° C. 16 gm (0.2 mole) of 50% aqueous sodium hydroxide. Allow to stir 1 hour at 25°–30° C. and separate layers. The organic layer is washed with 100 ml of water stripped to 100° C. under vacuum. The resulting product, 142 gm of colorless oil, has a refractive index of $n_D^{25}$ 1.5286. The structure is believed to be:

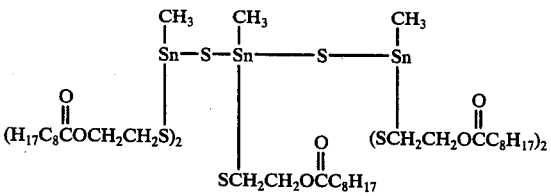

EXAMPLE 37

Into a 3-necked flask is placed 150.5 gms (0.5 mole) phenyltin trichloride, 300 ml of water, 400 ml of benzene and 218 gm (1.0 mole) 2-mercaptoethyl pelargonate. To the stirred mixture is added dropwise at 40° C. 80 gm (1.0 mole) of 50% aqueous sodium hydroxide. After allowing to stir for 1 hour at 40° C. is added dropwise 32.5 gm (0.25 mole) of 60% sodium sulfide dissolved in 75 ml of water. Allow to stir 1 hour at 40° C., separate layers and the organic phase is dried and stripped under vaccuum to 100° C. The resulting product, bis[monophenyl bis(2-mercaptoethyl pelargonate)] sulfide is obtained as 312 gms of a pale yellow oil. $n_D^{25}$ 1.5517.

EXAMPLE 38

Into a 2 liter flask is placed 120 gm (0.5 mole) of monomethyltin trichloride dissolved in 200 ml of water. Warmed to 30° C. and added 218 gm (1.0 mole) 2-mercaptoethyl pelargonate. Then is added dropwise, at 30°–40° C., 80 gm (1.0 mole) of 50% aqueous sodium hydroxide solution. The mixture is stirred for 1 hour. After this addition a solution formed by heating 32.5 gms (0.25 mole) of 60% sodium sulfide and 16 gms (0.5 mole) sulfur in 150 ml of water is added portionwise at 30°–40° C. Stir one hour after addition complete, then separate layers, wash the product layer with 200 ml of water. The organic phase is stripped to 100° C. under vacuum resulting in 296 gm pale yellow oil containing bis[monomethyltin bis(2-mercaptoethyl pelargonate)]-trisulfide. $n_D^{25}$ 1.5290.

EXAMPLE 39

Into a 3-necked flask is placed 169 gm (0.5 mole) monooctyltin trichloride, 300 ml of water, 400 ml of benzene and 204 gms (1.0 mole) 2-mercaptoethyl caprylate. The mixture is heated to 30°–40° C. and then is added dropwise 80 gms (1.0 mole) of 50% aqueous sodium hydroxide. Allow to stir for an hour under these conditions then add dropwise a solution of 32.5 gm (0.25 mole) of 60% aqueous Na$_2$S dissolved in 100 ml of water. Stir one hour after additon complete, separate layers and strip the organic phase to 100° C. under vacuum. The resulting pale yellow oil, 320 gms, is bis[monooctyltin bis(2-mercaptoethyl caprylate)]sulfide. $n_D^{25}$ 1.5144.

EXAMPLE 40

Into a 3-necked flask is placed 79.5 gms (0.33 mole) monomethyltin trichloride, 147.5 gm (0.67 mole) of dimethyltin dichloride dissolved in 250 ml of water, and 454 (1.33 moles) 2-mercaptoethyl oleate. Warmed to 30° C. and added dropwise 106 gm (1.33 mole) of 50% aqueous sodium hydroxide over a period of 1 hour at 30° C. Allow to stir 1 additional hour at this temperature. Then is added dropwise 65 gm (0.5 mole) of 60% sodium sulfide dissolved in 100 ml of water allowed to stir 1 hour after addition complete. The layers are separated and the organic layer washed with 200 ml of water and stripped to 100° C. under vacuum. The resulting product, 577 gms, is a yellow oil probably a mixture of bis[monomethyltin bis(2-mercaptoethyl oleate)]sulfide, bisdimethyltin mono(2-mercaptoethyl oleate)]sulfide and [monomethyltin bis(2-mercaptoethyl oleate)] [dimethyltin mono(2-mercaptoethyl oleate)] sulfide. $n_D^{25}$ 1.5070.

EXAMPLE 41

Into a 3-necked flask is placed 120 gm (0.5 mole) monomethyltin trichloride dissolved in 200 ml of water. Warmed to 30° C. and added 218 gm (1.0 mole) of 1-methyl-2-mercaptoethyl caprylate. Then added dropwise 80 gm (0.0 mole) of 50% aqueous sodium hydroxide at 30°–40° C, stirred for 1 hour after addition complete. Now is added dropwise 32.5 gm (0.25 mole) of 60% aqueous sodium sulfide in 100 ml of water at 25°–35°C, stir 1 hour and separate layers. The organic layer is washed with 200 ml of water and stripped under reduced pressure to yield 283 gm of nearly colorless oil. $n_D^{25}$ 1.5256. The product consists mostly of bis[monomethyltin bis(1mentyl-2-mercapto ethyl caprylate)]sulfide.

EXAMPLE 42

Into a 3-necked flask is placed 120 gms (0.5 mole) methyltin trichloride dissolved in 200 ml of water, 121 gms (1.0 mole) of 2-mercaptoethyl acetate after which there was slowly added 31 gm (0.50 mole) of 28% aqueous ammonium hydroxide. The mixture is stirred for 1 hour at reaction temperature of 30°–35° C. Then there is added 125 gm (0.25 mole) of 20% aqueous ammonium disulfide over a 60 minute period at 25°–35° C. The mixture is heated to 50° C. and the lower product layer separated from the aqueous phase. Washed the product with 200 ml of water and dried to 100° C. under reduced pressure. A 96% yield of pale yellow oil is obtained with refractive index at 25° C. of 1.5697. The yield is mainly bis[monomethyltin bis (2-mercaptoethyl acetate)]disulfide.

EXAMPLE 43

Into a 3-necked flask is placed 131 gm (0.6 mole) 2-mercaptoethyl caprylate, 61.5 gm (0.3 mole) of isooctylthioglycolate, 400 ml of toluene, 200 ml of water and 216 gm (0.9 mole) of monomethyltin trichloride. Cooled to 10° C. and added 64 gm (0.8 mole) of 50% aqueous sodium hydroxide at 10°–20° C. Stir 15 minutes and follow by adding 117 gms (0.9 mole) of 60% Na$_2$S in 150 ml of water over 30 minute period at 10°–20° C. Stir 15 minutes and finally add 8.0 gm (0.1 mole) of 50% aqueous NaOH and then stir and heat to 50° C. Separate the organic layer and strip under vacuum to 100° C. The yield, 315 gm of a viscous yellow oil, is believed to be mainly:

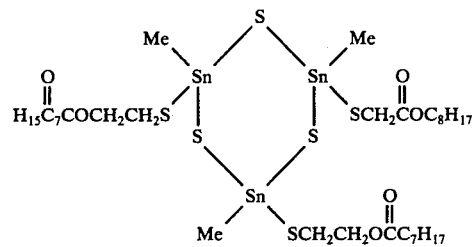

$n_D^{25}$ 1.5388.

EXAMPLE 44

Into a 3-necked flask is placed 181.5 gm (0.5 mole) of methylthiostannoic acid and 371.5 gms (0.5 mole) of methyltin tris(2-mercaptoethyl caprylate). The mixture is stirred and heated under nitrogen for 1.5 hours at 120° C. The product, a clear amber oil, was obtained in 96% yield. The product is believed to be:

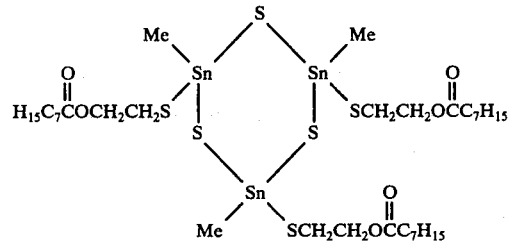

$n_D^{25}$ 1.5348.

EXAMPLE 45

Into a 3-necked flask is placed 120 gm (0.5 mole) of methyltin trichloride dissolved in 200 ml of water. Warmed to 30° C. and added 260 gm (1.0 mole) of 6-mercaptohexyl caprylate. Then add dropwise at 30–40° C. 80 gm (1.0 mole) of 50% aqueous NaOH solution. The mixture is stirred for 1 hour. After this addition, a solution of 32.5 gm (0.25 mole) of 60% aqueous sodium sulfide in 100 ml of water is added dropwise at 25°–35° C. After stirring for 1 hour at 35° C. the product layer is separated and washed with 200 ml of water. The product is then stripped to 100° C. under vacuum resulting in a 99% yield of pale yellow oil. $n_D^{25}$ 1.5345. The oil is believed to be bis[methyltin bis(6-mercaptohexyl caprylate)]sulfide.

EXAMPLE 46

Into a 2-liter flask is placed 120 gm (0.5 mole) of methyltin trichloride in 200 ml of water. Warmed to 30° C. and added 153 gm (0.75 mole) of 2-mercaptoethyl caprylate and 19.5 gms (0.25 mole) mercaptoethanol and 400 ml of toluene. Then added dropwise at 30°–40° C. 84 gm (1.0 mole) sodium bicarbonate dissolved in 250 ml of water. The mixture is stirred for 2 hours. At this time a solution of 32.5 gm (0.25 mole) 60% aqueous sodium sulfide in 100 ml of water is added dropwise at 35° C. Stirred 2 hours after addition complete, separated layers and the organic layer is stripped to 90° C. under vacuum resulting in 204 gms of a pale yellow oil. $n_D^{25}$ 1.5292. The product is believed to be mostly [monomethyltin(2-mercaptoethyl caprylate) (2-mercaptoethanol)] [monomethyltin bis(2-mercaptoethyl caprylate)]sulfide.

EXAMPLE 47

Into a 3-necked flask is placed 122.5 gm (0.5 mole) of butylchlorotin dihydroxide, 165 gms (0.5 mole) of 2-mercaptoethyl oleate and 750 ml of toluene. The mixture was refluxed until 8.5 ml of water was removed. The organic layer was stripped yielding 260 gms of a pale yellow oil. $n_D^{25}$ 1.5320. This product is believed to be bis[monobutylmonochlorotin(2-mercaptoethyl oleate)]oxide.

EXAMPLE 48

Into a 3-necked flask is placed 181.5 gm (0.50 mole) methylthiostannoic acid and 408 gm (2.0 mole) 2-mercaptoethyl caprylate and the mixture is heated and stirred at 90°–110° C for 1.5 hours under slightly reduced pressure. After this heating period the liquid is cooled and filtered at 40° C. The product, 571 gm, of a pale yellow oil has a refractive index at 25° C. of 1.5248.

EXAMPLE 49

Into a 3-necked flask is placed 360 gm (1.5 mole) of monomethyltin trichloride dissolved in 500 ml of water. Warmed to 30° C. and added 817 gm (4.0 mole) of 2-mercaptoethyl caprylate. Then added dropwise 320 gm (4.0 mole) of 50% aqueous sodium hydroxide at 30°–40° C. The mixture is stirred for 1 hour. After this addition, a solution of 32.5 gm (0.25 mole) of 60% sodium sulfide dissolved in 100 ml of water is added dropwise at 30°–40° C. After stirring for 1 hour at this temperature the product layer is separated and washed with 400 ml of water. The product is then stripped to 100° C. under vacuum resulting in 999 gm of nearly colorless oil. $n_D^{25}$ 1.5113.

EXAMPLE 50

Into a 3-necked flask is placed 555 gm (0.5 mole) of bis[methyltin bis(2-mercaptoethyl caprylate)]sulfide, 97 gm (0.5 mole) dimethyltin oxide and 400 ml of toluene. The mixture is stirred and heated at reflux for 2 hours during which time a clear solution is obtained. The solvent is removed under vacuum stripping yielding 650 gm of pale yellow oil. The reaction product contains [monomethyltin bis(2-mercaptoethyl caprylate)] [Monomethyltin mono(2-mercaptoethyl caprylate)-mono(2-mercaptoethyloxydimethyltin caprylate)]sulfide. $n_D^{25}$ 1.5289.

EXAMPLE 51

Into a 3-necked flask is placed 180 gm (0.75 mole) of monomethyltin trichloride dissolved in 300 ml of water warmed to 30° C. and added 306.5 gm (1.5 mole) of 2-mercaptoethyl caprylate. Then added dropwise 120 gms (1.5 mole) of 50% aqueous NaOH solution at 30°–40° C. The mixture is stirred for 1 hour. After this addition a solution of 16.3 gm (0.125 mole) of 60% sodium sulfide dissolved in 75 ml of water is added dropwise at 30°–40° C. After stirring for 1 hour at this temperature the product layer is separated and washed with 250 ml of water. The product is then stripped to 100° C. under vacuum resulting in 430 gm of pale yellow oil. The reaction product contains the following structures:

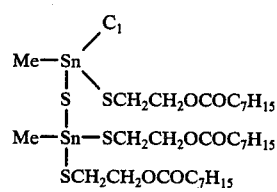

The refractive index of the mixture is 1.5151 at 25° C.

EXAMPLE 52

Into a 3-necked flask is placed 216 gm (0.9 mole) of methyltin trichloride, 22 gm (0.1 mole) of dimethyltin dichloride dissolved in 300 ml of water. Warmed to 30° C. and added 511 gm (2.5 mole) of 2-mercaptoethyl caprylate. Then added dropwise 200 gm (2.5 mole) of 50% aqueous sodium hydroxide at 30°–40° C. The mixture is stirred for 1 hour. After this addition, a solution of 26 gm (0.20 mole) of 60% aqueous sodium sulfide dissolved in 75 ml of water is added dropwise at 30°–40° C. After stirring for 1 hour, at this temperature, the product layer is separated and washed with 250 ml of water. The product is then stripped to 100° C. under vacuum resulting in 631 gms of colorless oil. $n_D^{25}$ 1.5153.

EXAMPLE 53

Into a 3-necked flask is placed 120 gm (0.5 mole) methyltintrichloride dissolved in 200 ml of water. Warmed to 30° C. and added 360 gm (1.0 mole) of monothioglycerine dicaprylate ester. Then added dropwise at 30°–40° C. 80 gm (1.0 mole) of 50% aqueous sodium hydroxide solution. The mixture is stirred for 1 hour. After this addition, a solution formed by heating 32.5 gm (0.25 mole) 60% aqueous $Na_2S$ and 8.0 gm (0.25 mole) sulfur in 100 ml of water, was added dropwise at 30°–40° C. After stirring for 1 hour at this temperature the product layer was separated and washed with 200 ml of water. The product was then stripped to 100° C. under vacuum resulting in a yield of 325 gm of yellow oil. $n_D^{25}$ 1.5143. The product is mainly bis[monomethyltin bis(thioglycerine dicaprylate)]disulfide.

EXAMPLE 54

Into a 3 necked flask is placed 110 gm (0.5 mole) of dimethyltin dichloride dissolved in 200 ml of water. Warmed to 30° C and added 109 gm (0.5 mole) 2-mercaptoethyl pelargonate. Then added dropwise at 30°–40° C, 40 gm (0.5 mole) of 50% aq. sodium hydroxide solution. The mixture is stirred for 1 hour. After this addition, a solution of 32.5 gms (0.25 mole) 60% aq. $Na_2S$ dissolved in 75 ml of water was added dropwise at 25°–35° C. After stirring for 1 hour at 35° C the product layer was separated and washed with 200 ml of water. The product was then stripped to 100° C under vacuum resulting in 95.5% of a pale yellow oil $n_D^{25}$ 1.5319. The product is mainly bis(dimethyltin mono [2-mercaptoethyl pelargonate]) sulfide.

EXAMPLE 55

Into a 2 liter flask is placed 60 gm (0.25 mole) monomethyltintrichloride, 55 gm (0.25 mole) dimethyltin dichloride dissolved in 200 ml of water. Warmed to 30° C and added 162 gm (0.75 mole) of 2-mercaptoethyl pelargonate after which there was slowly added 60 gm (0.75 mole) 50% aq. sodium hydroxide. The mixture is stirred for 1 hour. Then there is added 32.5g (0.25 mole) 60% aq. sodium sulfide dissolved in 75 ml of water. After stirring 1 hour at 35° C the layers are separated, the organic phase washed with 200 ml of water and dried under vacuum to 100° C. Obtained is 229 gm of a pale yellow oil $n_D^{25}$ 1.5296. The product consisted of a mixture of monomethyldimethyltin mono/di 2-mercaptoethyl pelargonate sulfide.

EXAMPLE 56

Bis(monomethyltin bis [2-mercaptoethyl pelargonate]) sulfide was mixed with the product prepared in Example 58, bis (dimethyltin mono [2-mercaptoethyl pelargonate]) sulfide in the ratio of 2/1, $n_D^{25}$ 1.5301.

The products of this invention, mercaptoalkylalkanoates, have the capability to react, with greater efficiency than the corresponding alkylthioalkanoates, with dialkyltin oxides and alkyl stannoic acids. Under reaction conditions where methyltin tris(alkylmercapto acetate or propionate) do not react at all with Bu$_2$SnO or Me$_2$SnO, the corresponding methyltin tris(2-mercaptoethylalkanoate) reacts completely after treatment of several hours at 80–120° C. The products are believed to have the formula:

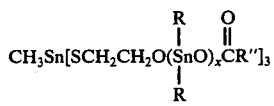

In order to illustrate the advantageous effects of the stabilizer compositions according to this invention, the following experiments were performed. All stabilizers used were evaluated on an equal cost not equal part basis. That is to say, certain stabilizers were used at higher part levels because their unit costs were lower. The tablets are also based on a substantially equal tin basis. The formulation of the PVC resin compositions in Tables I–VI is as follows:

| FORMULATION I | |
|---|---|
| Composition | Parts by Weight |
| Polyvinylchloride (PVC) | 100.0 |
| Omya 90$^T$ (fine particle size CaCO$_3$ coated with CaSt) | 1.0 |
| Titanium dioxide | 1.0 |
| Calcium Stearate (CaSt) | 0.6 |
| Paraffin Wax (Advawax 165) | 1.0 |
| AC 629A (oxidized low molecular weight ethylene homopolymer) | 0.1 |
| Stabilizer | as noted |

The resins from several major PVC producers were used to show the general response of the compounds of the invention to various PVC resins.

| PVC Resin | Manufacturer |
|---|---|
| PVC 450 (K=64.3) | Diamond Shamrock |
| Geon 103 EP (K=62.2–64.3) | B. F. Goodrich |
| Q-SAN-7 (K=65.8) | Union Carbide |
| Allied SR 414-3 (K=64.7) | Universal PVC Resin |

Stability Test (Dynamic Mill Stability)

The stabilizer is blended with the PVC resin composition on a two roll mill, at 380° F., a temperature at which the mix is fluid and thorough blending facilitated, masticating the mixture at 380° F. and sampling at 1 minute intervals after first introduction of the mix to the mill.

The appearance of the samples resulting from the dynamic mill stability test is given in Tables I through IV, the sample numbers are the same throughout the tables.

TABLE I

Resin Allied SR-414-3
Dynamic Mill Stability
380° F, 30/40 RPM
(minutes)

| Sample No. | Tin Contained (mg) | 1 | 2 | 3 | 4 | 5 | 6 | 7 | 8 | 9 | 10 |
|---|---|---|---|---|---|---|---|---|---|---|---|
| 7 | 28.0 | 10+ | 10 | 9 | 8+ | 8 | 6 | 5 | 4 | 2 | 1 |
| 2 | 30.7 | 10 | 9 | 8+ | 8 | 7 | 6 | 5 | 4 | 2 | 1 |
| 1 | 33.5 | 10 | 9 | 8+ | 8 | 7 | 6+ | 5+ | 4 | 2 | 1 |
| 9 | 28.4 | 10+ | 10 | 9 | 9 | 8+ | 7 | 6 | 5 | 3 | 1 |
| 17 | 32.5 | 10 | 9 | 8+ | 8 | 7 | 6+ | 5+ | 4 | 2 | 1 |
| 18 | 28.4 | 10+ | 10 | 9 | 9 | 8+ | 7 | 6 | 5 | 3 | 1 |
| 4 | 36.0 | 9+ | 8 | 7 | 6+ | 6 | 5 | 4 | 3 | 1 | 1 |
| 19 | 35.0 | 10+ | 10 | 9 | 9 | 8+ | 7 | 6 | 5 | 2 | 1 |

Color Scale:
10(white) - 5(tan-orange) - 0(burn) (intensity, not hue)

Sample:
17. Thermolite 136 Butyltin 85% mono/15% di part isooctyl thioglycolate part —S— linkage part unreacted chloride diluted to 12.8% tin
18. 2/3 monomethyl tris(2-mercaptoethyl oleate) and 1/3 bis[monoethyltin bis(2-mercaptoethly oleate)]sulfide.
19. bis[methyltin di(2-mercaptoethyl pelargonate)]sulfide.

TABLE II

Resin B.F. Goodrich Geon 103 EP
Dynamic Mill Stability
380° F., 30/40 RPM
(minutes)

| Sample No. | Tin Contained (mg.) | 1 | 2 | 3 | 4 | 5 | 6 | 7 | 8 | 9 | 10 |
|---|---|---|---|---|---|---|---|---|---|---|---|
| 1 | 33.5 | 10 | 9+ | 9 | 8 | 7 | 6 | 5 | 3 | 2 | 2 |
| 3 | 34.0 | 10+ | 10+ | 10 | 9+ | 8 | 5 | 2 | 1 | 0 | 0 |
| 4 | 36.0 | 9+ | 8 | 7 | 6+ | 5+ | 5 | 4 | 3 | 2 | 2 |
| 6 | 33.6 | 10+ | 10+ | 10+ | 10 | 9+ | 8 | 6 | 5 | 3 | 1 |
| 2 | 30.7 | 10 | 9 | 8 | 7 | 6 | 5 | 4 | 3 | 2 | 1 |
| 7 | 28.0 | 10+ | 10 | 9+ | 9 | 7 | 6 | 5 | 3 | 1 | 1 |

TABLE II-continued

Resin B.F. Goodrich Geon 103 EP
Dynamic Mill Stability
380° F., 30/40 RPM
(minutes)

| Sample No. | Tin Contained (mg.) | 1 | 2 | 3 | 4 | 5 | 6 | 7 | 8 | 9 | 10 |
|---|---|---|---|---|---|---|---|---|---|---|---|
| 5 | 26.3 | 9 | 8 | 6+ | 5+ | 5 | 4 | 2 | 2 | 1 | 1 |
| 8 | 25.8 | 10 | 9+ | 9 | 7 | 5+ | 4 | 2 | 2 | 1 | 1 |

Color Scale: 10(white) - 5(tan-orange) - 0(burn)

Sample:
1. Cardinal AC-78   Butyltin 85% mono/15% di part isooctyl thioglycolate parts —S—linkage diluted to 13.4% tin with dioctyl phthalate.
2. ⅔ monomethyltin tris isooctyl thioglycolate in ⅓ bis[monomethyltin bis(isooctyl thioglycolate)]disulfide (70%) + mineral oil (30%)
3. bis[methyltin di(2-mercaptoethyl tallate)]sulfide.
4. Mark 1905   methyltin 50% mono/50% di part isooctyl thioglycolate —S—linkage plus diluent, 14.4% tin
5. Butyltin tris isooctylthioglycolate.
6. Bis[monomethyltin bis(2-mercaptoethyl phenyl acetate)] sulfide.
7. ⅔ monomethyltin tris(2-mercaptoethyl pelargonate) and ⅓ bis [monomethyltin bis(2-mercaptoethyl pelargonate)] sulfide (70%) and mineral oil (30%).
8. butyltin tris(2-mercaptoethyl pelargonate)

TABLE III

Resin Union Carbide Q-SAN-7
Dynamic Mill Stability
380° F, 30/40 RPM
(minutes)

| Sample No. | Tin Contained (mg.) | 1 | 2 | 3 | 4 | 5 | 6 | 7 | 8 | 9 | 10 |
|---|---|---|---|---|---|---|---|---|---|---|---|
| 9 | 28.4 | 10 | 10 | 9 | 8 | 7+ | 6 | 5+ | 4 | 3 | 2 |
| 10 | 25.3 | 9 | 8+ | 8 | 7 | 6 | 5 | 4 | 3 | 2 | 1 |
| 11 | 31.0 | 9 | 8 | 7 | 5 | 4 | 3 | 3 | 2 | 2 | 2 |
| 12 | 29.0 | 10 | 9+ | 9 | 8 | 7 | 6 | 5 | 3 | 1 | 1 |
| 13 | 35.0 | 10+ | 10+ | 10 | 9 | 8 | 7+ | 6 | 5 | 3 | 2 |
| 14 | 35.8 | 9 | 8 | 7 | 6 | 5 | 5 | 4 | 2 | 2 | 2 |
| 15 | 35.0 | 10 | 10 | 9 | 7 | 5+ | 5 | 4 | 2 | 2 | 2 |
| 16 | 33.0 | 8 | 7 | 6 | 5 | 4 | 3 | 3 | 2 | 2 | 2 |

Color Scale: 10(white) - 5 (tan-orange) - 0(burn)

Sample:
9. 2/3 monomethyltin tris(2-mercaptoethyl stearate) and 1/3 bis[monomethyltin bis(2-mercaptoethyl stearate)] sulfide
10. methyltin tris(2-mercaptoethyl pelargonate)
11. Mark 1909, (same as No. 4 without diluent) 20% tin
12. Same formulation as No. 10.
13. bis[monomethyltin bis(2-mercaptoethyl stearate)]sulfide.
14. dimethyltin bis(isooctyl thioglycolate)
15. dimethyltin bis(2-mercaptoethyl pelargonate).
16. dibutyltin bis(isooctyl thioglycolate).

Sample:
20. bis[methyltin bis(isooctyl thioglycolate)]disulfide.
21. bis[monomethyltin bis(2-mercaptoethyl oleate)]sulfide.

In plant pipe extrusion test, the compounds of the present invention proved superior stabilizers to commercially available tin stabilizers and furnished outstanding white pipe at equivalent output rates. Both dynamic mill stability (DMS) and residual oven stability tests were run on the formulations.

TABLE IV

Resin Diamond Shamrock PVC 450
Dynamic Mill Stability
380° F, 30/40 RPM
(minutes)

| Sample No. | Tin Contained (mg.) | 1 | 2 | 3 | 4 | 5 | 6 | 7 | 8 | 9 | 10 |
|---|---|---|---|---|---|---|---|---|---|---|---|
| 13 | 35.0 | 10+ | 10+ | 10+ | 10+ | 10 | 9 | 8 | 7 | 4 | 2 |
| 20 | 36.7 | 10 | 9 | 8 | 8 | 7 | 6 | 4 | 3 | 2 | 1 |
| 21 | 35.0 | 10+ | 10+ | 10+ | 10 | 9 | 8 | 7 | 6 | 4 | 3 |
| 7 | 28.0 | 10+ | 10+ | 10+ | 10 | 9 | 7 | 6 | 4 | 2 | 1 |
| 2 | 30.7 | 10 | 9 | 8 | 7 | 6 | 5 | 4 | 3 | 2 | 1 |
| 1 | 33.5 | 10 | 9 | 8 | 7 | 6 | 5 | 4 | 3 | 2 | 1 |
| 9 | 28.4 | 10+ | 10+ | 10 | 9+ | 9 | 8 | 7 | 4 | 2 | 1 |
| 17 | 32.5 | 10 | 9+ | 8+ | 7 | 6 | 5 | 4 | 3 | 2 | 1 |

Color Scale: 10(white) - 5(tan-orange) - 0(burn) (intensity, not hue)

The formulation was the same as that used in Table I through IV using Allied SR 414-3 as the vinyl chloride resin. The amounts of stabilizer were as indicated in Tables V and VI. The amounts chosen were designed to have about the same amount of tin in the formulations. The Sample numbers are the same as in Tables I through IV with the additional numbers noted under Table V.

TABLE V

1. RESIDUAL PIPE STABILITY, 375° F.

| Sample Blend | phr | 0' | 2' | 4' | 6' | 8' | 10' | 14' | 16' | 18' | 20' |
|---|---|---|---|---|---|---|---|---|---|---|---|
| 2 | 0.25 | 10 | 10 | 10 | 9+ | 9 | 8 | 7 | 7 | 6 | 5 | 4 |
| 17 | 0.25 | 9+ | 9+ | 9+ | 9 | 9 | 7+ | 6 | 6 | 5 | 5 | 4 |
| 22 | 0.25 | 10 | 10 | 10 | 10 | 10 | 8 | 7 | 7 | 6 | 5 | 4 |
| 23 | 0.175 | 10 | 10 | 10 | 9+ | 9+ | 8 | 7 | 7 | 6 | 5 | 4 |
| 4 | 0.25 | 9+ | 9+ | 9 | 8+ | 8 | 7+ | 7 | 6+ | 6 | 5 | 4 |
| 11 | 0.15 | 9 | 9 | 9 | 8 | 8 | 7 | 6 | 6 | 5 | 4 | 4 |
| 1 | 0.25 | 9+ | 9+ | 9+ | 9 | 8 | 7 | 7 | 7 | 6 | 5 | 5 |
| 7 | 0.25 | 10+ | 10+ | 10+ | 10+ | 10 | 9 | 8 | 7 | 7 | 6 | 5 |
| 24 | 0.175 | 10+ | 10+ | 10+ | 10+ | 10+ | 10 | 9 | 8 | 7 | 6+ | 5 |
| 19 | 0.175 | 10+ | 10+ | 10+ | 10+ | 10+ | 10 | 9 | 7+ | 7+ | 6+ | 6 |
| 25 | 0.175 | 10+ | 10+ | 10+ | 10+ | 10 | 10 | 8 | 7 | 7 | 6 | 5+ |

COLOR SCALE: 10(white - 5(orange) - 0(burn)

Sample:
22. Thermolite 138 a commercial methyltin product.
23. Thermolite 148 a commercial methyltin product
24. 2/3 monomethyltin tris(2-mercaptoethyl pelargonate) in 1/3 bis[monomethyltin bis(2-mercaptoethyl-pelargonate)] sulfide
25. 2/3 monomethyltin tris(2-mercaptoethyl laurate) in 1/3 bis[monomethyltin bis(2-mercaptoethyl laurate)]sulfide

TABLE VI

2. MILL STABILITY OF PIPE BLENDS 380° F, 30/40 RPM

| Sample Blend | phr | 1' | 2' | 3' | 4' | 5' | 6' | 7' | 8' | 9' |
|---|---|---|---|---|---|---|---|---|---|---|
| 2 | 0.25 | 10 | 9 | 8 | 7 | 6 | 5 | 4 | 2 | 1 |
| 17 | 0.25 | 10 | 8+ | 7 | 6 | 5 | 4+ | 3 | 1 | 1 |
| 22* | 0.25 | 10 | 9 | 8 | 7 | 6 | 5 | 4 | 2 | 1 |
| 23 | 0.175 | 10 | 9 | 9 | 8 | 7 | 6 | 4 | 3 | 1 |
| 4 | 0.25 | 9 | 8 | 7 | 6 | 5+ | 4 | 3 | 2 | 1 |
| 11 | 0.15 | 9 | 7 | 6 | 5+ | 5 | 4 | 2 | 1 | 1 |
| 1 | 0.25 | 10 | 9 | 8 | 7 | 6 | 5 | 4 | 1 | 1 |
| 7 | 0.25 | 10+ | 9+ | 8 | 7 | 6 | 5 | 4 | 2 | 1 |
| 24 | 0.175 | 10+ | 9 | 8 | 6+ | 5+ | 5 | 4 | 1 | 1 |
| 19 | 0.175 | 10+ | 9+ | 9 | 8 | 7 | 5+ | 4 | 2 | 1 |
| 25 | 0.175 | 10+ | 8 | 6+ | 5+ | 4 | 3 | 1 | 1 | 1 |

COLOR SCALE: 10(white - 5(orange) - 0(burn)
*22 - slight grey contamination

Mixtures of monoalkyltin compounds and dialkyltin compounds of the present invention appear to be more efficacious than the single components, whether prepared together from the chlorides or simply mixed as can be seen from Table VII

TABLE VII

FORMULATION II, RESIN B. F. GOODRICH GEON 103EP
Dynamic Mill Stability 380° F 30/40 RPM (minutes)

| Sample NO. | Tin Contained (mg.) | 2 | 3 | 4 | 5 | 6 | 7 | 8 | 9 | 10 |
|---|---|---|---|---|---|---|---|---|---|---|
| 19 | 150 | 10+ | 10 | 9 | 8 | 7 | 7 | 6 | 4+ | 3 | 1+ |
| 26 | 150 | 9+ | 9 | 9 | 7+ | 6+ | 6 | 5 | 4 | 3 | 2 |
| 27 | 150 | 10+ | 10 | 10 | 9+ | 9 | 8+ | 8 | 6+ | 5+ | 3 |
| 27* | 150 | 10+ | 10 | 10 | 9+ | 9 | 8+ | 8 | 6 | 5 | 3 |
| 28 | 150 | 10+ | 10 | 9 | 8+ | 8 | 6+ | 5+ | 3+ | 2 | 1 |
| 29 | 150 | 10+ | 10 | 9+ | 9 | 8+ | 7 | 6 | 5 | 4 | 3 |
| 30 | 150 | 10+ | 10 | 9 | 8+ | 7+ | 7 | 5+ | 4 | 4 | 3 |
| 31 | 150 | 9+ | 9 | 8+ | 8 | 7 | 5+ | 4 | 3+ | 3 | 2 |

Color Scale: 10 (white) - 5 (Tan-Orange) - 0 (Burn)

Sample:
26. bis (dimethyltin mono [2-mercaptoethyl pelargonate]) sulfide
27. 2/3 bis (monomethyltin bis [2-mercaptoethyl pelargonate]) sulfide and 1/3 bis (dimethyltin mono [2-mercaptoethyl pelargonate]) sulfide. Prep. by Example 50.
27*. Prepared by Example 55.
28. 1/3 bis (monomethyltin bis [2-mercaptoethyl pelargonate]) sulfide and 2/3 bis (dimethyltin mono [2-mercaptoethyl pelargonate]) sulfide.
29. 1/3 dimethyltin bis [2-mercaptoethyl pelargonate] and 2/3 bis (methyltin bis [2-mercaptoethyl pelargonate]) sulfide.
30. 2/3 monomethyltin tris (2-mercaptoethyl pelargonate) and 1/3 bis (dimethyltin mono [2-mercaptoethyl pelargonate]) sulfide.
31. 1/3 dimethyltin bis (2-mercaptoethyl pelargonate) and 2/3 monomethyltin tris (2-mercaptoethyl pelargonate).

What is claimed is:

1. A monoorganotin or diorganotin mercaptoalkyl ester of a carboxylic acid or mercapto hydroxyalkyl ester of a carboxylic acid mono or poly sulfide useful as a stabilizer for improving the resistance to deterioration of vinyl chloride polymers when heated at 350° F, containing at least one tin atc having one to two hydrocarbyl groups having from 1 to 20 carbon atoms and selected from the group consisting of alkyl, aryl, cycloalkyl, aralkyl and alkenyl and linked to the tin through carbon, at least one mercaptoalkyl ester of a carboxylic acid group linked to tin through the sulfur of the mercaptoalkyl group and at least one mono or polysulfide sulfur group bonded exclusively to tin, the organotin compound having an amount of tin within the range from 10 to 42% by weight and an amount of sulfur within the range from 8 to 42% by weight.

2. An organotin compound according to claim 1, having the formula:

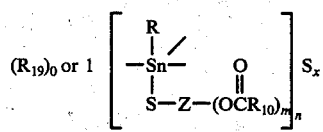

wherein R is alkyl, aryl, cycloalkyl, aralkyl or alkenyl of 1 to 20 carbon atms, $R_{19}$ is R or

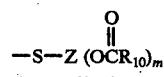

where Z is a polyvalent alkylene or hydroxy-alkylene radical of at least 2 carbon atoms, the valency of Z being $m + 1$ $R_{10}$ is hydrogen, hydrocarbyl of 1 to 19 carbon atoms wherein the hydrocarbyl is alkyl, aryl, aralkyl, cycloalkyl, aralkenyl or alkenyl having up to 3 ethylene double bonds, hydroxyalkyl of up to 19 carbon atoms, hydroxyalkenyl of up to 19 carbon atoms, m is an integer of 1 to 3, n is an integer from 1 to 2 and x is 1 to 10.

3. An organotin compound according to Claim 1 (A) having the formula:

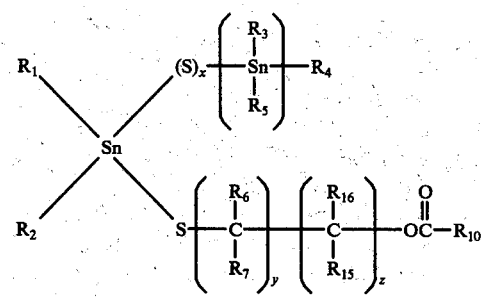

where x is a number from 1 to 10, $R_1$, $R_2$, $R_3$, $R_4$, $R_5$ and $R_9$ are alkyl, aryl, cycloalkyl, aralkyl or alkenyl of 1 to 20 carbon atoms,

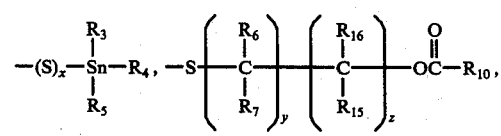

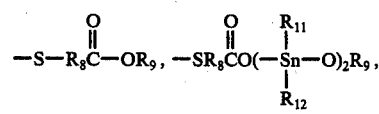

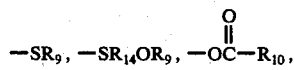

atomic weight 35 to 127, $R_6$ and $R_{16}$ are hydrogen, hydroxyl,

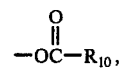

alkyl of 1 to 18 carbon atoms, $R_7$ and $R_{15}$ are hydrogen or alkyl of 1 to 18 carbon atoms, y is at least 1, z is 0 or an integer and the total carbon atoms in

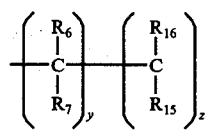

is 2 to 20, $R_{10}$ is hydrogen, hydrocarbyl of 1 to 19 carbon atoms wherein the hydrocarbyl group is alkyl, aryl, aralkyl, cycloalkyl, aralkenyl, or alkenyl having up to 3 ethylenic double bonds, hydroxyalkyl of up to 19 carbon atoms or hydroxyalkenyl of up to 19 carbon atoms, $R_8$ is alkylene of 1 to 20 carbon atoms or such a group having a halo or hydroxy substituent or an ethylenically unsaturated divalent aliphatic hydrocarbon or hydroxy hydrocarbon group having 2 to 19 carbon atoms, $R_{11}$ and $R_{12}$ are alkyl, aryl, cycloalkyl, aralkyl or alkenyl having 1 to 20 carbon atoms and $R_{14}$ is alkylene of 2 to 20 carbon atoms with the proviso that at least one of $R_1$, $R_2$, $R_3$ and $R_4$ is hydrocarbyl, or (B) the overbased reaction product of a compound of formula I with a dialkyltin oxide having 1 to 20 carbon atoms in the alkyl groups, or a monoalkyltin oxide, or an alkyl stannoic acid.

4. An organotin compound according to claim 1 having the formula:

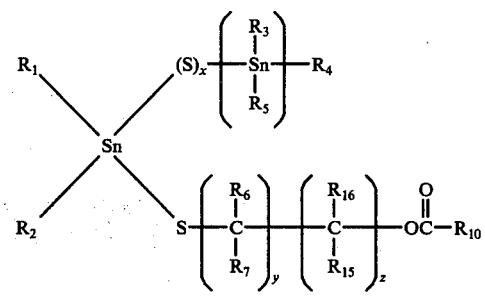

where x is a number from 1 to 10, $R_1$, $R_2$, $R_3$, $R_4$, $R_5$ and $R_9$ are alkyl, aryl, cycloalkyl, aralkyl or alkenyl of 1 to 20 carbon atoms,

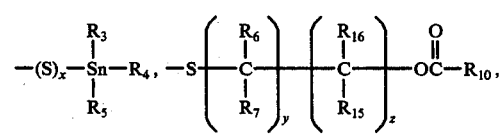

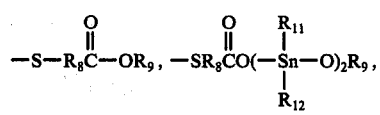

$R_6$ and $R_{16}$ are hydrogen, hydroxyl,

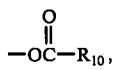

alkyl of 1 to b 18 carbon atoms, $R_7$ and $R_{15}$ are hydrogen or alkyl of 1 to 18 carbon atoms, $y^x$ is at least 1, Z is 0 or an integer and the total of $y$ and Z in

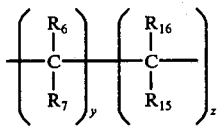

is 2 to 20, $R_{10}$ is hydrogen, hydrocarbyl of 1 to 19 carbon atoms wherein the hydrocarbyl group is alkyl, aryl, aralkyl, cycloalkyl, aralkenyl, or alkenyl having up to 3 ethylenic double bonds, hydroxyalkyl of up to 19 carbon atoms or hydroxyalkenyl of up to 19 carbon atoms, $R_8$ is alkylene of 1 to 20 carbon atoms or such a group having a halo or hydroxy substituent or an ethylenically unsaturated divalent aliphatic hydrocarbon or hydroxy hydrocarbon group having 2 to 19 carbon atoms, $R_{11}$ and $R_{12}$ are alkyl, aryl, cycloalkyl, aralkyl or alkenyl having 1 to 20 carbon atoms and $R_{14}$ is alkylene of 2 to 20 carbon atoms with the proviso that at least one of $R_1$, $R_2$, $R_3$ and $R_4$ is hydrocarbyl.

5. An organotin compound according to claim 1 (A) having the formula:

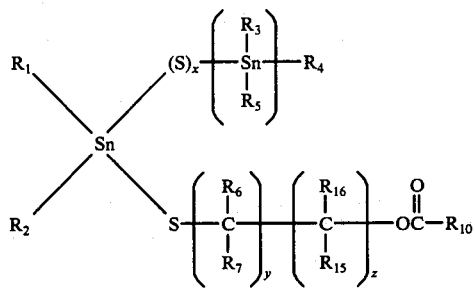

where z is a number from 1 to 10, $R_1$, $R_2$, $R_3$, $R_4$, $R_5$ and $R_9$ are alkyl, aryl, cycloalkyl, aralkyl or alkenyl of 1 to 20 carbon atoms,

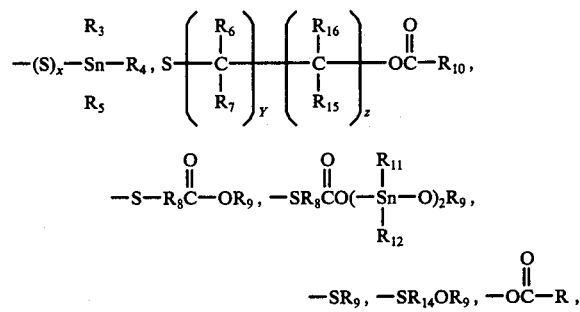

$R_6$ and $R_{16}$ are hydrogen, hydroxyl,

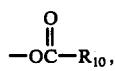

alkyl of 1 to 18 carbon atoms, $R_7$ and $R_{15}$ are hydrogen or alkyl of 1 to 18 carbon atoms, $y$ is at least 1, $z$ is 0 or an integer and the total of $y$ and $z$ in

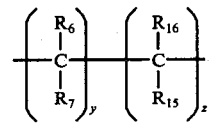

is 2 to 20, $R_{10}$ is hydrogen, hydrocarbyl of 1 to 19 carbon atoms wherein the hydrocarbyl group is alkyl, aryl, aralkyl, cycloalkyl, aralkenyl, or alkenyl having up to 3 ethylenic double bonds, hydroxyalkyl of up to 19 carbon atoms or hydroxyalkenyl of up to 19 carbon atoms, $R_8$ is alkylene of 1 to 20 carbon atoms or such a group having a halo or hydroxy substituent or an ethylenically unsaturated divalent aliphatic hydrocarbon or hydroxy hydrocarbon group having 2 to 19 carbon atoms, $R_{11}$ and $R_{12}$ are alkyl, aryl, cycloalkyl, aralkyl or alkenyl having 1 to 20 carbon atoms and $R_{14}$ is alkylene of 2 to 20 carbon atoms with the proviso that at least one of $R_1$, $R_2$, $R_3$ and $R_4$ is hydrocarbyl, or (B) the overbased reaction product of a compound of formula I with a dialkyltin oxide having 1 to 20 carbon atoms in the alkyl group, or a monoalkyltin oxide, or an alkyl stannoic acid.

6. An organotin sulfide according to claim 1 which is a mono to tetrasulfide.

7. An organotin sulfide according to claim 6 which is a mono to disulfide.

8. An organotin sulfide according to claim 7 which is a monosulfide.

9. An organotin sulfide according to claim 7 which is a disulfide.

10. An organotin compound according to claim 6 which is a monoorganotin compound.

11. An organotin compound according to claim 6 which is a diorganotin compound.

12. An organotin compound according to claim 6 which is a mixed mono and diorganotin compound.

13. An organotin compound according to claim 6 which is an overbased reaction product with a dialkyltin oxide having 1 to 20 carbon atoms in the alkyl groups, or a monoalkyltinoxide or alkyl stannoic acid.

14. An organotin compound according to claim 1 having the formula:

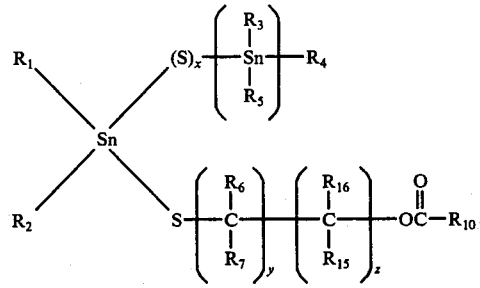

where $x$ is a number from 1 to 10, $R_1$, $R_2$, $R_3$, $R_4$, $R_5$, and $R_9$ are alkyl, aryl, cycloalkyl, aralkyl or alkenyl of 1 to 20 carbon atoms,

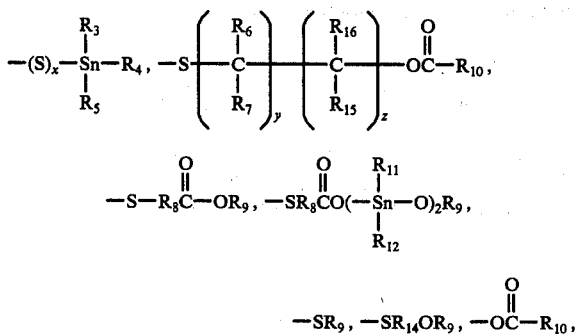

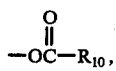

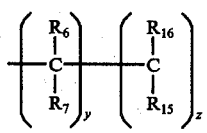

atomic weight 35 to 127, $R_6$ and $R_{16}$ are hydrogen, hydroxyl, $$-OC-R_{10},$$
(with O double-bonded)

alkyl of 1 to 18 carbon atoms, $R_7$ and $R_{15}$ are hydrogen or alkyl of 1 to 18 carbon atoms, $y$ is at least 1, Z is 0 or an integer and the total of $y$ and $z$ in

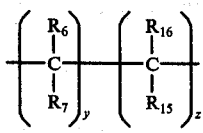

is 2 to 20, $R_{10}$ is hydrogen, hydrocarbyl of 1 to 19 carbon atoms wherein the hydrocarbyl group is alkyl, aryl, aralkyl, cycloalkyl, aralkenyl, or alkenyl having up to 3 ethylenic double bonds, hydroxyalkyl of up to 19 carbon atoms or hydroxyalkenyl of up to 19 carbon atoms, $R_8$ is alkylene of 1 to 20 carbon atoms or such a group having a halo or hydroxy substituent or an ethylenically unsaturated divalent aliphatic hydrocarbon or hydroxy hydrocarbon group having 2 to 19 carbon atoms, $R_{11}$ and $R_{12}$ are alkyl, aryl, cycloalkyl, aralkyl or alkenyl having 1 to 20 carbon atoms and $R_{14}$ is alkylene of 2 to 20 carbon atoms with the proviso that at least one of $R_1$, $R_2$, $R_3$ and $R_4$ is hydrocarbyl.

15. An organotin compound according to claim 4, wherein $R_5$ is other than hydrocarbyl, $x$ is a number from 1 to 4, $R_6$ is hydrogen or alkyl of 1 to 18 carbon atoms, $R_8$ is alkylene of 1 to 20 carbon atoms or an ethylenically unsaturated divalent aliphatic hydrocarbon group.

16. An organotin compound according to claim 15 where at least one of $R_1$ and $R_2$ is hydrocarbyl and at least one of $R_3$ and $R_4$ is hydrocarbyl.

17. An organotin compound according to claim 12 wherein when $R_1$, $R_2$, $R_3$ and $R_4$ are hydrocarbyl, the hydrocarbyl is methyl.

18. An organotin compound according to claim 15 wherein

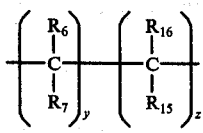

is alkylene of 2 to 3 carbon atoms.

19. An organotin compound according to claim 18 wherein $R_{10}$ is alkyl of 6 to 19 carbon atoms, alkenyl of 17 carbon atoms or hydroxyalkenyl of 17 carbon atoms.

20. An organotin compound according to claim 19 wherein when $R_1$, $R_2$, $R_3$ and $R_4$ are hydrocarbyl, the hydrocarbyl is methyl.

21. An organotin compound according to claim 20 wherein $x$ is 1 to 2.

22. An organotin compound according to claim 21, wherein $x$ is 1.

23. A compound according to claim 4 which is a bis monoalkyltin di(mercaptoalkylalkanoate) mono to disulfide wherein the mercaptoalkyl has 2 to 3 carbon atoms and the alkanoate has 6 to 20 carbon atoms.

24. A compound according to claim 23 wherein the monoalkyltin is monomethyltin.

25. A compound according to claim 23 wherein the mercaptoalkyl is mercaptoethyl and the alkanoate has 7 to 18 carbon atoms.

26. A compound according to claim 4 which is a bis monoalkyltin di(mercaptoalkylalkenoate) mono to disulfide wherein the mercaptoalkyl has 2 to 3 carbon atoms and the alkenoate has 18 carbon atoms and 1 to 3 double bonds.

27. A compound according to claim 26 wherein the monoalkyltin is monomethyltin.

28. A compound according to claim 4 which is a bis monoalkyltin di(mercaptoalkylricinoleate) wherein the mercaptoalkyl has 2 to 3 carbon atoms.

29. A compound according to claim 28 wherein the monoalkyltin is monomethyltin.

30. A compound according to claim 4 which is monoalkyltin di[(mercaptoalkyl alkanoate)] [dialkyltin mono(mercaptoalkyl alkanoate)] mono to disulfide wherein the mercaptoalkyl groups have 2 to 3 carbon atoms and the alkanoate group has 2 to 20 carbon atoms.

31. A compound according to claim 30 wherein the monoalkyltin is monomethyltin and the dialkyltin is dimethyltin.

32. A compound according to claim 31 wherein the alkanoate group has 7 to 18 carbon atoms.

33. A compound according to claim 4 which is monoalkyltin di[(mercaptoalkyl alkenoate or ricinoleate)] [dialkyltin mono(mercaptoalkyl alkenoate or ricinoleate)] mono to disulfide wherein the mercaptoalkyl groups have 2 to 3 carbon atoms and the alkenoate has 18 carbon atoms.

34. A compound according to claim 33 wherein the monoalkyltin is monomethyltin and the dialkyltin is dimethyltin.

35. A compound according to claim 4 which is bis[monoalkyl/dialkyltin mono/di(mercapto 2 to 3 carbon atom alkyl alkanoate or alkenoate or ricinoleate)] mono to disulfide.

36. A compound according to claim 35 wherein the alkanoate has 7 to 18 carbon atoms and the alkenoate has 18 carbon atoms and 1 to 3 double bonds.

37. A compound according to claim 35 wherein the monoalkyltin is monomethyltin and the dialkyltin is dimethyltin.

38. A compound according to claim 4 which is [monoalkyl monochlorotin mercapto 2 to 3 carbon atom alkyl alkanoate or alkenoate] [monoalkyltin bis(mercapto 2 to 3 carbon atom alkyl alkanoate or alkenoate)] mono to disulfide, the alkanoate group has 2 to 20 carbon atoms and the alkenoate has 18 carbon atoms and 1 to 3 double bonds.

39. A compound according to claim 4 which is a [monoalkyltin bis(mercapto 2 to 3 carbon atom alkyl alkanoate or alkenoate)] [monoalkyltin mono(mercapto 2 to 3 carbon atom alkyl alkanoate or alkenoate)-monoalkyl mercaptide] mono to disulfide wherein the alkanoate group has 2 to 20 carbon atoms and the alkenoate has 18 carbon atoms and 1 to 3 double bonds.

40. A compound according to claim 4 which is a [monoalkyltin bis(mercapto 2 to 3 carbon atom alkyl alkanoate or alkenoate or ricinoleate)] [monoalkyltin mono(2-mercapto 2 to 3 carbon atom alkyl) monoalkyl or alkenyl thio 2 to 3 carbon atom alkanoate] mono or disulfide.

41. A compound according to claim 40 wherein the alkanoate has 7 to 18 carbon atoms and the alkenoate has 18 carbon atoms.

42. A compound according to claim 41 wherein the monoalkyltin is monomethyltin.

43. A compound according to claim 42 wherein the alkyl or alkenylthio 2 to 3 carbon atom alkanoate group has 8 to 18 carbon atoms in the alkyl group or 18 carbon atoms in the alkenyl group.

44. A compound according to claim 4 which is a [monoalkyltin bis(mercapto 2 to 3 carbon atom alkyl alkanoate, alkenoate or ricinoleate)] [monoalkyltin mono(mercapto 2 to 3 carbon atom alkyl alkanoate, alkenoate or ricinoleate) monoalkyl ester of an alkendioic acid, an alkanedioic acid or a phthalic acid] mono to disulfide wherein the alkanoate has 7 to 20 carbon atoms and the alkenoate has 18 carbon atoms and 1 to 3 double bonds.

45. A compound according to claim 4 which is a [monoalkyltin bis(mercapto 2 to 3 carbon atom alkyl alkanoate, alkenoate or ricinoleate) monoalkyl or alkenyl thio 2 to 3 carbon atom alkanoate] mono or disulfide.

46. A compound according to claim 4 which is a [monoalkyltin bis(mercapto 2 to 3 carbon atom alkyl alkanoate, alkenoate or ricinoleate)] [monoalkyltin (alkyl or alkenyl thio 2 to 3 carbon atom alkanoate) (mercapto 2 to 3 carbon atom alkanoate)] mono or disulfide.

47. A compound according to claim 4 which is selected from the group consisting of (1) bis [monoalkyltin bis(mercapto 2 to 3 carbon atom alkyl alkanoate, alkenoate or ricinoleate)] sulfide or disulfide, (2) bis [dialkyltin mono(mercapto 2 to 3 carbon atom alkyl alkanoate, alkenoate or ricinoleate)] sulfide or disulfide and (3) [monoalkyltin bis(mercapto 2 to 3 carbon atom alkyl alkanoate, alkenoate or ricinoleate)] [dialkyltin mono(mercapto 2 to 3 carbon atom alkyl alkanoate, alkenoate or ricinoleate)] sulfide or disulfide.

48. A compound according to claim 47 having formula (1).

49. A compound according to claim 47 having formula (2).

50. A compound according to claim 47 having formula (3).

51. A compound according to claim 1 having the formula:

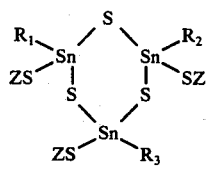

where $R_1$, $R_2$ and $R_3$ are alkyl, aryl, cycloalkyl, aralkyl or alkenyl of 1 to 20 carbon atoms and Z is

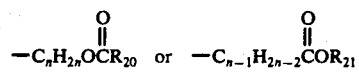

where $n$ is 2 or 3, $R_{20}$ is alkyl, alkenyl, aryl or aralkyl of 1 to 19 carbon atoms and $R_{21}$ is alkyl or alkenyl of 1 to 20 carbon atoms with the proviso that at least one Z is

52. A compound according to claim 51 wherein $R_{20}$ is alkyl of 7 to 17 carbon atoms or alkenyl of 18 carbon atoms.

53. A compound according to claim 52 wherein $R_1$, $R_2$ and $R_3$ are all methyl.

54. A compound according to claim 15 wherein there is present at least one thio 2 to 3 carbon atom alkanoate alkyl ester group attached to tin directly by the sulfur atom.

55. An organic compound according to claim 2 where X is 1 to 4 and Z has 2 to 20 carbon atoms.

56. A mixture of two sulfides according to claim 1, said mixture containing at least one monoorganotin sulfide and at least one diorganotin sulfide.

57. A mixture according to claim 56 wherein the monoorganotin sulfide is 96 to 50% and the diorganotin sulfide is 4 to 50% of the total weight of mono and diorganotin sulfides.

58. An organotin compound which is a bis[(monoalkyltin) bis merceptoalkylester of a carboxylic acid)] oxide or a bis[(monoalkylmonohalotin) mono(mercaptoalkylester of a carboxylic acid)] oxide.

59. A compound according to claim 55 wherein $n$ is 2 and wherein one of the two

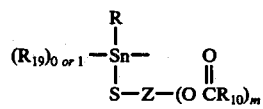

groups is

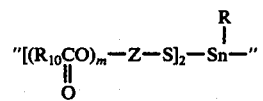

and the second is

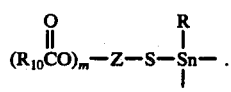

60. A compound according to claim 59 wherein said second group is

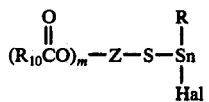

where Hal is halogen of atomic weight 35 to 127.

61. A compound according to claim 14 wherein one of $R_1$ and $R_2$ is halogen of atomic weight 35 to 127.

* * * * *

Disclaimer 4,062,881.—*Thomas G. Kugele*, Cincinnati, Ohio. SULFIDE CONTAINING TIN STABILIZERS. Patent dated Dec. 13, 1977. Disclaimer filed July 5, 1978, by the assignee, *Cincinnati Milacron Chemicals, Inc.*

Hereby enters this disclaimer to claims 2, 45, 55, 59 and 60 of said patent.

[*Official Gazette August 29, 1978.*]

UNITED STATES PATENT OFFICE
CERTIFICATE OF CORRECTION

Patent No. 4,062,881  Dated December 13, 1977

Inventor(s) Thomas G. KUGELE

It is certified that error appears in the above-identified patent and that said Letters Patent are hereby corrected as shown below:

Claim 1 col. 28 line 68 change "atc" to "atom"
Claim 3 col. 30 line 1 before "atomic" insert "halogen of"
Claim 3 col. 30 line 10 change "carbon atoms" to "of y and z"
Claim 4 col. 31 line 7 change "yx" to "y"
Claim 4 col. 31 line 8 change "Z" to "z"
Claim 5 col. 31 line 46 change "z" to "x"
Claim 5 col. 31 line 52 change the first formula to read

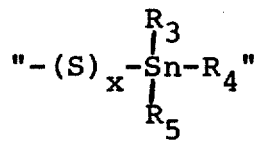

"$-(S)_x-\underset{\underset{R_5}{|}}{\overset{\overset{R_3}{|}}{Sn}}-R_4$"

UNITED STATES PATENT OFFICE
CERTIFICATE OF CORRECTION

Patent No. 4,062,881        Dated December 13, 1977

Inventor(s) Thomas G. KUGELE

It is certified that error appears in the above-identified patent and that said Letters Patent are hereby corrected as shown below:

Claim 5 col. 31 line 61 change the last formula to read

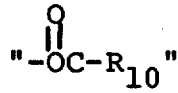

Claim 14 col. 33 line 16 before "atomic" insert "halogen of"
Claim 14 col. 33 line 24 change "Z" to "z"
Claim 17 col. 33 line 55 change "12" to "16"
Claim 38 col. 34 line 62 change "4" to "3"
Claim 60 col. 36 line 60 rewrite the formula

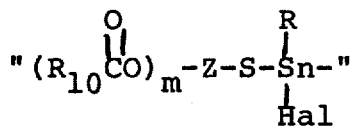

Signed and Sealed this

Fourth Day of March 1980

[SEAL]

Attest:

SIDNEY A. DIAMOND

Attesting Officer    Commissioner of Patents and Trademarks

UNITED STATES PATENT AND TRADEMARK OFFICE
CERTIFICATE OF CORRECTION

PATENT NO. : 4,062,881
DATED : December 13, 1977
INVENTOR(S) : Thomas G. Kugele

It is certified that error appears in the above—identified patent and that said Letters Patent is hereby corrected as shown below:

Col. 3, line 1 that portion of the formula reading:

```
    R                           R
    |                           |
  - Sn -     should read     -- Sn --
    |                           |
    S                           S
```

Claim 2, Col. 29, line 13 that portion of the formula reading:

```
    R  /                        R  /
    | /                         | /
  - Sn -     should read     -- Sn --
    |                           |
    S                           S
```

Signed and Sealed this

Fourth Day of April, 1989

*Attest:*

*Attesting Officer*

DONALD J. QUIGG

*Commissioner of Patents and Trademarks*

REEXAMINATION CERTIFICATE (1179th)

United States Patent [19]

Kugele

[11] B1 4,062,881

[45] Certificate Issued Dec. 26, 1989

[54] SULFIDE CONTAINING STABILIZERS

[75] Inventor: Thomas G. Kugele, Cincinnati, Ohio

[73] Assignee: Morton Thiokol Inc.

Reexamination Request:
No. 90/001,534, Jun. 21, 1988

Reexamination Certificate for:
Patent No.: 4,062,881
Issued: Dec. 13, 1977
Appl. No.: 492,969
Filed: Jul. 26, 1974

[51] Int. Cl.⁴ ............... C08H 3/00; C07F 7/22
[52] U.S. Cl. ............... 260/399; 524/182; 556/83; 556/84; 556/89; 556/91; 556/93
[58] Field of Search ............ 260/399; 556/89, 91, 556/92, 93; 524/182

[56] References Cited

U.S. PATENT DOCUMENTS 3,609,120  9/1971  Hoye et al. ............ 524/182
3,764,571 10/1973  Jennings et al. ........ 524/180
4,345,045  8/1982  Jennings et al. ........ 524/180

FOREIGN PATENT DOCUMENTS 1236925 of 0000  United Kingdom ........ 260/399
1008845 11/1965  United Kingdom ........ 524/180

OTHER PUBLICATIONS

S. A. Riethmayer, Organostannic Stabilizing Agents for PVC and the Sulfuric Acid–Oxygen Synergy Between Organostanoaliphatic Acid Salts and Organostanomercaptides, Kunststoff-Rundschau, No. 7, Jul. 1963, pp. 345–352 (Original German text and English translation).
H. Verity Smith, The Development of the Organotin Stabilizers, Tin Research Institute, Dec. 1959.

*Primary Examiner*—A. McFarlane

[57] ABSTRACT

A polyvinyl chloride resin stabilizer is provided having a high concentration of tin, in the range from about 10% to about 42% by weight, and a high concentration of sulfur, within the range from about 8% to about 42% sulfur, comprising at least one monoorganotin or diorganotin mercapto alkanol carboxylic ester (or mercapto alkyl carboxylate), mono or poly sulfide and preferably mixed monoorganotin and diorganotin mercaptoalkyl carboxylic acid ester sulfides, especially having 4 to 50% of the diorganotin compound. Polyvinyl chloride resin compositions are also provided, containing these compounds.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1, 3–44, 46–54, 56–58 and 61 is confirmed.

Claims 2, 45, 55, 59 and 60 were previously disclaimed.

* * * * *